United States Patent
Halterman

(10) Patent No.: US 9,205,129 B2
(45) Date of Patent: Dec. 8, 2015

(54) METHODS OF TREATMENT AND SCREENING ASSAYS FOR HIF-1α REGULATION

(75) Inventor: Marc Halterman, Penfield, NY (US)

(73) Assignee: University of Rochester, Rochester, NY (US)

( * ) Notice: Subject to any disclaimer, the term of this patent is extended or adjusted under 35 U.S.C. 154(b) by 512 days.

(21) Appl. No.: 13/501,066

(22) PCT Filed: Oct. 8, 2010

(86) PCT No.: PCT/US2010/052031
§ 371 (c)(1),
(2), (4) Date: Jun. 13, 2012

(87) PCT Pub. No.: WO2011/044492
PCT Pub. Date: Apr. 14, 2011

(65) Prior Publication Data
US 2012/0251629 A1    Oct. 4, 2012

Related U.S. Application Data

(60) Provisional application No. 61/250,281, filed on Oct. 9, 2009.

(51) Int. Cl.
*A61K 38/17* (2006.01)

(52) U.S. Cl.
CPC .................................. *A61K 38/1703* (2013.01)

(58) Field of Classification Search
None
See application file for complete search history.

(56) References Cited

U.S. PATENT DOCUMENTS

| | | | |
|---|---|---|---|
| 2005/0202450 A1* | 9/2005 | Huang | 435/6 |
| 2006/0270699 A1* | 11/2006 | Guenzler-Pukall et al. | 514/291 |
| 2008/0213404 A1* | 9/2008 | Johnson et al. | 424/725 |
| 2013/0158010 A1* | 6/2013 | Shalwitz et al. | 514/212.08 |

OTHER PUBLICATIONS

HEK-293, ATCC Product Sheet, 2014.*
HEP-3B, ATCC Product Sheet, 2014.*
MKP-1, Uniprot Entry, 2014.*
BNIP3, Uniprot Entry, 2014.*
NOXA, Uniprot Entry, 2014.*
Zhang et al. "Treatment with siRNA and Antisense Oligonucleotides Targeted to HIF-1alpha Induced Apoptosis in Human Tongue Squamous Cell Carcinomas," Int J Cancer 111(6):849-857 (2004).
Hasegawa et al. Therapeutic Time Window and Dose Dependence of Neuroprotective Efects of Sodium Orthovanadate Following Transient Middle Cerebral Artery Occlusion in Rats. J. Pharm Exp Ther 317(2):875-881 (2006).
Liu et al. "Supression of the Dual-Specificity Phosphatase MKP-1 Enhances HIF-1 Trans-activation and Increases Expression of EPO," Biochem Biophys Res Comm 312(3):780-786 (2003).
Huang et al. "Leu-574 of HIF-1 Alpha is Essential for the von Hippel-Lindau (VHL)-mediated Degradation Pathway," J Biol Chem 277(44):41750-41755 (2002).
Mylonis et al. "Identification of MAPK Phosphorylation Sites and Their Role in the Localization and Activity of Hypoxia-inducible Factor-1alpha," J Biol Chem 281(44):33095-33106 (2006).
Metzen et al. "Nitric Oxide Impairs Normoxic Degradation of HIF-1alpha by Inhibition of Prolyl Hydroxylases," Mol Bio Cell 14:3470-3481 (2003).
Choi et al. "Clioquinol, a Cu(II)/Zn(II) Chelator, Inhibits Both Ubiquitination and Asparagine Hydroxylation of Hypoxia-inducible Factor-1alpha, Leading to Expression of Vascular Endothelial Growth Factor and Erythropoietin in Normoxic Cells," J Biol Chem 281(45):34056-34063 (2006).
Semenza "Defining the Role of Hypoxia-inducible Factor 1 in Cancer Biology and Therapeutics," Oncogene ePub 29 (5):625-634 (2009).
Pugh et al. "Regulation of Angiogenesis by Hypoxia: Role of the HIF System," Nature Med 9(6):677-684 (2003).
ISA210 International Search Report for PCT/US2010/052031 mailed Feb. 8, 2011.
ISA237 International Written Opinion for PCT/US2010/052031 mailed Feb. 8, 2011.

* cited by examiner

*Primary Examiner* — Taeyoon Kim
*Assistant Examiner* — Srikanth Patury
(74) *Attorney, Agent, or Firm* — LeClairRyan, a Professional Corporation

(57) ABSTRACT

The present invention relates to a method of treating a patient for a condition where blood flow to a tissue or organ is interrupted. This method involves administering to a patient with a hypoxic condition where blood flow to a tissue or organ is interrupted, or at risk thereof, a compound that reduces the rate of HIF-1α inactivation in cells affected by the condition, thereby treating the patient for the condition. Also disclosed is a method of treating a tumor in a patient. In addition, the present invention relates to methods of identifying compounds as candidate drugs for treatment of hypoxic conditions and for treating tumors in a subject.

13 Claims, 8 Drawing Sheets

A

Cells: N2A
WB: V5

1 control psG5/pUb6 DMSO
2 control psG5/mHIF DMSO
3 pSG5-MKPwt/mHIF DMSO
4 control psG5/pUb6 MG132
5 control psG5/mHIF MG132
6 pSG5-MKPwt/mHIF MG132

B

Cells: N2A
WB: V5

1 Crude - pUb6 - MG132
2 Crude - hHIF MG132

C

N2As
IP: HIS, WB: HIF

1. Crude pUb6-MCS / MG132
2. Crude pUb6-hHIF / MG132
3. Purified pUb6-MCS / MG132
4. Purified pUb6-hHIF / MG132

A

```
Sequence Coverage: 14%

Matched peptides shown in Bold

1 MEGAGGANDK KKISSERRKE KSRDAARSRR SKESEVFYEL ANQLPLPHNV
  51 SSHLDKASVM RLTISYLRVR KLLDAGDLDI EDDMKAQMNC FYLKALDGFV
 101 MVLTDDGDMI YISDNVNKYM GLTQFELTGH SVFDFTHPCD HEEMREMLTH
 151 RNGLVKKGKE QNTQRSFFLR MKCTLTSRGR TMNIKSATWK VLHCTGHIHV
 201 YDTNSNQPQC GYKKPPMTCL VLICEPIPHP SNIEIPLDSK TFLSRHSLDM
 251 KFSYCDERIT ELMGYEPEEL LGRSIYEYYH ALDSDHLTKT HHDMFTKGQV
 301 TTGQYRMLAK RGGYVWVETQ ATVIYNTKNS QPQCIVCVNY VVSGIIQHDL
 351 IFSLQQTECV LKPVESSDMK MTQLFTKVES EDTSSLFDKL KKEPDALTLI
 401 APAAGDTIIS LDFGSNDTET DDQQLEEVPL YNDVMLPSPN EKLQNINLAM
 451 SPLPTAETPK PLRSSADPAL NQEVALKLEP NPESLELSFT MPQIQDQTPS
 501 PSDGSTRQSS PEPNSPSEYC FYVDSDMVNE FKLELVEKLF AEDTEAKNPF
 551 STQDTDLDLE MLAPYIPMDD DLQLRSFDQL SPLESSSASP ESASPQSTVT
 601 VFQQTQIQEP TANATTTTAT TDELKTVTKD RMEDIKILIA SPSPTHIHKE
 651 TTSATSSPYR DTQSRTASPN RAGKGVIEQT EKSHPRSPNV LSVALSQRTT
 701 VPEEELNPKI LALQNAQRKR KMEHDGSLFQ AVGIGTLLQQ PDDHAATTSL
 751 SWKRVKGCKS SEQNGMEQKT IILIPSDLAC RLLGQSMDES GLPQLTSYDC
 801 EVNAPIQGSR NLLQGEELLR ALDQVN
```

B

```
Sequence Coverage: 4%

Matched peptides shown in Bold

1 MEGAGGANDK KKISSERRKE KSRDAARSRR SKESEVFYEL ANQLPLPHNV
  51 SSHLDKASVM RLTISYLRVR KLLDAGDLDI EDDMKAQMNC FYLKALDGFV
 101 MVLTDDGDMI YISDNVNKYM GLTQFELTGH SVFDFTHPCD HEEMREMLTH
 151 RNGLVKKGKE QNTQRSFFLR MKCTLTSRGR TMNIKSATWK VLHCTGHIHV
 201 YDTNSNQPQC GYKKPPMTCL VLICEPIPHP SNIEIPLDSK TFLSRHSLDM
 251 KFSYCDERIT ELMGYEPEEL LGRSIYEYYH ALDSDHLTKT HHDMFTKGQV
 301 TTGQYRMLAK RGGYVWVETQ ATVIYNTKNS QPQCIVCVNY VVSGIIQHDL
 351 IFSLQQTECV LKPVESSDMK MTQLFTKVES EDTSSLFDKL KKEPDALTLI
 401 APAAGDTIIS LDFGSNDTET DDQQLEEVPL YNDVMLPSPN EKLQNINLAM
 451 SPLPTAETPK PLRSSADPAL NQEVALKLEP NPESLELSFT MPQIQDQTPS
 501 PSDGSTRQSS PEPNSPSEYC FYVDSDMVNE FKLELVEKLF AEDTEAKNPF
 551 STQDTDLDLE MLAPYIPMDD DLQLRSFDQL SPLESSSASP ESASPQSTVT
 601 VFQQTQIQEP TANATTTTAT TDELKTVTKD RMEDIKILIA SPSPTHIHKE
 651 TTSATSSPYR DTQSRTASPN RAGKGVIEQT EKSHPRSPNV LSVALSQRTT
 701 VPEEELNPKI LALQNAQRKR KMEHDGSLFQ AVGIGTLLQQ PDDHAATTSL
 751 SWKRVKGCKS SEQNGMEQKT IILIPSDLAC RLLGQSMDES GLPQLTSYDC
 801 EVNAPIQGSR NLLQGEELLR ALDQVN
```

*FIG. 8*

SEQUENCE LISTING

```
<160> NUMBER OF SEQ ID NOS: 7

<210> SEQ ID NO 1
<211> LENGTH: 20
<212> TYPE: DNA
<213> ORGANISM: Artificial
<220> FEATURE:
<223> OTHER INFORMATION: Primer

<400> SEQUENCE: 1
```

```
agacaacgcg ggcaccgatt                                               20

<210> SEQ ID NO 2
<211> LENGTH: 24
<212> TYPE: DNA
<213> ORGANISM: Artificial
<220> FEATURE:
<223> OTHER INFORMATION: Primer

<400> SEQUENCE: 2
tcagttaact tgatccaaag ctct                                          24

<210> SEQ ID NO 3
<211> LENGTH: 63
<212> TYPE: DNA
<213> ORGANISM: Artificial
<220> FEATURE:
<223> OTHER INFORMATION: Primer

<400> SEQUENCE: 3
gcgggatcca tggaacaaaa actcatctca gaagaagatc tgagttctga acgtcgaaaa   60
gaa                                                                 63

<210> SEQ ID NO 4
<211> LENGTH: 54
<212> TYPE: DNA
<213> ORGANISM: Artificial
<220> FEATURE:
<223> OTHER INFORMATION: Primer

<400> SEQUENCE: 4
ggggcggccg ctaacttgat ccaaagctct gagtaattct tcaccctgca gtag         54

<210> SEQ ID NO 5
<211> LENGTH: 825
<212> TYPE: PRT
<213> ORGANISM: Homo sapiens

<400> SEQUENCE: 5

Met Glu Gly Ala Gly Gly Ala Asn Asp Lys Lys Ile Ser Ser Glu Arg
1               5                   10                  15

Arg Lys Glu Lys Ser Arg Asp Ala Ala Arg Ser Arg Arg Ser Lys Glu
            20                  25                  30

Ser Glu Val Phe Tyr Glu Leu Ala His Gln Leu Pro Leu Pro His Asn
        35                  40                  45

Val Ser Ser His Leu Asp Lys Ala Ser Val Met Arg Leu Thr Ile Ser
    50                  55                  60

Tyr Leu Arg Val Arg Lys Leu Leu Asp Ala Gly Asp Leu Asp Ile Glu
65                  70                  75                  80

Asp Asp Met Lys Ala Gln Met Asn Cys Phe Tyr Leu Lys Ala Leu Asp
                85                  90                  95

Gly Phe Val Met Val Leu Thr Asp Asp Gly Asp Met Ile Tyr Ile Ser
            100                 105                 110

Asp Asn Val Asn Lys Tyr Met Gly Leu Thr Gln Phe Glu Leu Thr Gly
        115                 120                 125

His Ser Val Phe Asp Phe Thr His Pro Cys Asp His Glu Glu Met Arg
    130                 135                 140

Glu Met Leu Thr His Arg Asn Gly Leu Val Lys Lys Gly Lys Glu Gln
145                 150                 155                 160

Asn Thr Gln Arg Ser Phe Phe Leu Arg Met Lys Cys Thr Leu Thr Ser
```

-continued

```
                165                 170                 175
Arg Gly Arg Thr Met Asn Ile Lys Ser Ala Thr Trp Lys Val Leu His
                    180                 185                 190

Cys Thr Gly His Ile His Val Tyr Asp Thr Asn Ser Asn Gln Pro Gln
                    195                 200                 205

Cys Gly Tyr Lys Lys Pro Pro Met Thr Cys Leu Val Leu Ile Cys Glu
                    210                 215                 220

Pro Ile Pro His Pro Ser Asn Ile Glu Ile Pro Leu Asp Ser Lys Thr
225                 230                 235                 240

Phe Leu Ser Arg His Ser Leu Asp Met Lys Phe Ser Tyr Cys Asp Glu
                    245                 250                 255

Arg Ile Thr Glu Leu Met Gly Tyr Glu Pro Glu Glu Leu Leu Gly Arg
                    260                 265                 270

Ser Ile Tyr Glu Tyr Tyr His Ala Leu Asp Ser Asp His Leu Thr Lys
                    275                 280                 285

Thr His His Asp Met Phe Thr Lys Gly Gln Val Thr Thr Gly Gln Tyr
                    290                 295                 300

Arg Met Leu Ala Lys Arg Gly Gly Tyr Val Trp Val Glu Thr Gln Ala
305                 310                 315                 320

Thr Val Ile Tyr Asn Thr Lys Asn Ser Gln Pro Gln Cys Ile Val Cys
                    325                 330                 335

Val Asn Tyr Val Val Ser Gly Ile Ile Gln His Asp Leu Ile Phe Ser
                    340                 345                 350

Leu Gln Gln Thr Glu Cys Val Leu Lys Pro Val Glu Ser Ser Asp Met
                    355                 360                 365

Lys Met Thr Gln Leu Phe Thr Lys Val Glu Ser Glu Asp Thr Ser Ser
                    370                 375                 380

Leu Phe Asp Lys Leu Lys Lys Glu Pro Asp Ala Leu Thr Leu Leu Ala
385                 390                 395                 400

Pro Ala Ala Gly Asp Thr Ile Ile Ser Leu Asp Phe Gly Ser Asn Asp
                    405                 410                 415

Thr Glu Thr Asp Asp Gln Gln Leu Glu Glu Val Pro Leu Tyr Asn Asp
                    420                 425                 430

Val Met Leu Pro Ser Pro Asn Glu Lys Leu Gln Asn Ile Asn Leu Ala
                    435                 440                 445

Met Ser Pro Leu Pro Thr Ala Glu Thr Pro Lys Pro Leu Arg Ser Ser
                    450                 455                 460

Ala Asp Pro Ala Leu Asn Gln Glu Val Ala Leu Lys Leu Glu Pro Asn
465                 470                 475                 480

Pro Glu Ser Leu Glu Leu Ser Phe Thr Met Pro Gln Ile Gln Asp Gln
                    485                 490                 495

Thr Pro Ser Pro Ser Asp Gly Ser Thr Arg Gln Ser Ser Pro Glu Pro
                    500                 505                 510

Asn Ser Pro Ser Glu Tyr Cys Phe Tyr Val Asp Ser Asp Met Val Asn
                    515                 520                 525

Glu Phe Lys Leu Glu Leu Val Glu Lys Leu Phe Ala Glu Asp Thr Glu
                    530                 535                 540

Ala Lys Asn Pro Phe Ser Thr Gln Asp Thr Asp Leu Asp Leu Glu Met
545                 550                 555                 560

Leu Ala Pro Tyr Ile Pro Met Asp Asp Asp Leu Gln Leu Arg Ser Phe
                    565                 570                 575
```

```
Asp Gln Leu Ser Pro Leu Glu Ser Ser Ala Ser Pro Glu Ser Ala
            580                 585                 590
Ser Pro Gln Ser Thr Val Thr Val Phe Gln Gln Thr Gln Ile Gln Glu
            595                 600                 605
Pro Thr Ala Asn Ala Thr Thr Thr Thr Ala Thr Thr Asp Glu Leu Lys
            610                 615                 620
Thr Val Thr Lys Asp Arg Met Glu Asp Ile Lys Ile Leu Ile Ala Ser
625                 630                 635                 640
Pro Ser Pro Thr His Ile His Lys Glu Thr Thr Ser Ala Thr Ser Ser
                    645                 650                 655
Pro Tyr Arg Asp Thr Gln Ser Arg Thr Ala Ser Pro Asn Arg Ala Gly
                    660                 665                 670
Lys Gly Val Ile Glu Gln Thr Glu Lys Ser His Pro Arg Ser Pro Asn
                    675                 680                 685
Val Leu Ser Val Ala Leu Ser Gln Arg Thr Thr Val Pro Glu Glu Glu
            690                 695                 700
Leu Asn Pro Lys Ile Leu Ala Leu Gln Asn Ala Gln Arg Lys Arg Lys
705                 710                 715                 720
Met Glu His Asp Gly Ser Leu Phe Gln Ala Val Gly Ile Gly Thr Leu
                    725                 730                 735
Leu Gln Gln Pro Asp Asp His Ala Ala Thr Thr Ser Leu Ser Trp Lys
                    740                 745                 750
Arg Val Lys Gly Cys Lys Ser Ser Glu Gln Asn Gly Met Glu Gln Lys
            755                 760                 765
Thr Ile Ile Leu Ile Pro Ser Asp Leu Ala Cys Arg Leu Leu Gly Gln
770                 775                 780
Ser Met Asp Glu Ser Gly Leu Pro Gln Leu Thr Ser Tyr Asp Cys Glu
785                 790                 795                 800
Val Asn Ala Pro Ile Gln Gly Ser Arg Asn Leu Leu Gln Gly Glu Glu
                    805                 810                 815
Leu Leu Arg Ala Leu Asp Gln Val Asn
            820                 825

<210> SEQ ID NO 6
<211> LENGTH: 7
<212> TYPE: PRT
<213> ORGANISM: Homo sapiens

<400> SEQUENCE: 6

Asn Gln Glu Val Ala Leu Lys
1               5

<210> SEQ ID NO 7
<211> LENGTH: 9
<212> TYPE: PRT
<213> ORGANISM: Homo sapiens

<400> SEQUENCE: 7

Leu Phe Ala Glu Asp Thr Glu Ala Lys
1               5
```

METHODS OF TREATMENT AND SCREENING ASSAYS FOR HIF-1α REGULATION

This application claims the benefit of U.S. Provisional Patent Application Ser. No. 61/250,281, filed Oct. 9, 2009, which is hereby incorporated by reference in its entirety.

This invention was made with government support under National Institute of Health Grant No. K99-NS 060764. The government has certain rights in the invention.

FIELD OF THE INVENTION

The present invention relates generally to methods of treatment and screening assays for HIF-1alpha ("HIF-1α") regulation.

BACKGROUND OF THE INVENTION

The proper growth and development of multi-cellular organisms is closely linked with cellular metabolic activity and reserve. The mismatch between metabolic supply and demand also provides many cues directing the developmental programs vital for the proper formation and function of organ systems characteristic of more complex organisms. In the central nervous system, hypoxic gradients regulate stem and neural progenitor cell survival, stimulate cell surface molecules involved in migration, and serve to fine tune the process of naturally occurring cell death through the regulated expression of neurotrophic factors (Nyakas et al., "Hypoxia and Brain Development," *Prog. Neurobiol.* 49:1-51 (1996); Chen et al., "Hypoxic Microenvironment Within an Embryo Induces Apoptosis and is Essential for Proper Morphological Development," *Teratology* 60:215-25 (1999); Rees et al., "Fetal and Neonatal Origins of Altered Brain Development," *Early Hum. Dev.* 81:753-61 (2005); Pocock, "Oxygen Levels Affect Axon Guidance and Neuronal Migration in *Caenorhabditis elegans*," *Nat. Neurosci.* 11:894-900 (2008)). Mild ischemia stimulates transcriptional programs that specify increased efficiency in energy utilization and activates pathways that enhance resistance to oxidant stress (Gidday, "Cerebral Preconditioning and Ischeamic Tolerance," *Nat. Rev. Neurosci.* 7:437-48 (2006)). However, prolonged stress can overwhelm such innate, adaptive responses resulting in the activation of a pathological program of autophagy and delayed neuronal apoptosis (Dirnagl et al., "Pathobiology of Ischaemic Stroke: An Integrated View," *Trends Neurosci.* 22:391-97 (1999)). Understanding the factors involved in regulating the balance between adaptive and pathological transcription could have far reaching implications in the fields of developmental neuroscience, cancer, and stroke therapeutics.

The basic helix loop helix transcription factor hypoxia-inducible-factor-1-α ("HIF-1α") (GenBank Accession No. AAH12527) is central to the cellular physiological response to hypoxia and controls the expression of a broad array of genes (Semenza, "Targeting HIF-1 for Cancer Therapy," *Nat. Rev. Cancer* 3:721-32 (2003)). HIF-1α plays a critical role in regulating the balance between oxidative phosphorylation and glycolysis, regulates oxygen sensing at the carotid body, and stimulates expansion of red cell mass through the transcriptional regulation of erythropoietin. In this regard, HIF-1α serves as a master vertical integrator functioning at multiple levels including the cellular, tissue, organ system, and whole organism level. Not surprising, loss of HIF-1α function results in embryonic lethality due largely to abnormalities in placental development and mesenchymal cell survival (Iyer et al., "Cellular and Developmental Control of $O_2$ Homeostasis by Hypoxia-Inducible Factor 1 alpha," *Genes Dev.* 12:149-62 (1998) and Kotch et al., "Defective Vascularization of HIF-1alpha-null Embryos is Not Associated with VEGF Deficiency but With Mesenchymal Cell Death," *Dev. Biol.* 209:254-67 (1999)). In the case of ischemic stroke, HIF-1α appears to play a more complex role (Halternan et al., "Hypoxia-Inducible Factor-1alpha Mediates Hypoxia-Induced Delayed Neuronal Death that Involves p53," *J. Neurosci.* 19:6818-24 (1999); Helton et al., "Brain-Specific Knock-Out of Hypoxia-Inducible Factor-1alpha Reduces Rather Than Increases Hypoxic-Ischemic Damage," *J. Neurosci.* 25:4099-4107 (2005); Baranova et al., "Neuron-Specific Inactivation of the Hypoxia Inducible Factor 1 Alpha Increases Brain Injury In a Mouse Model of Transient Focal Cerebral Ischemia," *J. Neurosci.* 27:6320-32 (2007)). In certain contexts, HIF-1α supports cell death signaling in neurons in concert with factors including p53 resulting in the transactivation of pro-apoptotic genes (An et al., "Stabilization of Wild-Type p53 by Hypoxia-Inducible Factor 1 Alpha," *Nature* 392:405-08 (1998); Bruick, "Expression of the Gene Encoding the Proapoptic Nip3 Protein is Induced by Hypoxia," *Proc. Nat'l Acad. Sci.* 97:9082-87 (2000); Kim et al., "BH3-Only Protein Noxa is a Mediator of Hypoxic Cell Death Induced by Hypoxia-Inducible Factor 1alpha," *J. Exp. Med.* 199:113-24 (2004)). The molecular basis regarding HIF-1α transcriptional switching behavior remains incompletely defined.

The dual activity phosphatase MKP1/DUSP1 is regulated by hypoxia (Seta et al., "Hypoxia-Induced Regulation of MAPK Phosphatase-1 as Identified by Subtractive Suppression Hybridization and cDNA Microarray Analysis," *J. Biol. Chem.* 276:44405-12 (2001)), and has been linked to the post-translational modification of HIF-1α. Like other immediate early genes including FOS and Jun, MKP-1 expression is induced early after transient forebrain ischemia in the adult (Takano et al., "Induction of CL100 Protein Tyrosine Phosphatase Following Transient Forebrain Ischemia In the Rat Brain," *J. Cereb. Blood Flow Metab.* 15:33-4; Wiessner et al., "Transient Forebrain Ischemia Induces an Immediate-Early Gene Encoding the Mitogen-Activated Protein Kinase Phosphatase 3CH134 In the Adult Rat Brain," *Neuroscience* 64:959-66 (1995); Nagata et al., "Profiling of Genes Associated With Transcriptional Responses In Mouse Hippocampus After Transient Forebrain Ischemia Using High-Density Oligonucleotide DNA Array," *Brain Res. Mol. Brain. Res.* 121: 1-11 (2004)). DUSP1 responds to oxidative stress under the transcriptional control of E2F-1 and p53 (Yang et al., "p53 Transactivates the Phosphatase MKP1 Through Both Intronic and Exonic p53 Responsive Elements," *Cancer Biol. Ther.* 3:1277-82 (2004); Wu et al., "The Noncatalytic Amino Terminus of Mitogen-Activated Protein Kinase Phosphatase 1 Directs Clear Targeting and Serum Response Element Transcriptional Regulation," *Mol. Cell. Biol.* 25:4792-4803 (2005); Wang et al., "Dual Specificity Phosphatase 1/CL100 is a Direct Transcriptional Target of E2F-1 in the Apoptopic Response to Oxidative Stress," *Cancer Res.* 67:6737-44 (2007)). DUSP1 promotes cellular differentiation (Sakaue et al., "Role of MAPK Phosphatase-1 (MKP-1) In Adipocyte Differentiation," *J. Biol. Chem.* 279:39951-57 (2004)), and reports suggest that it mediates the adaptive response of neural cells to ischemic injury (Kwak et al., "Isolation and Characterization of a Human Dual Specificity Protein-Tyrosine Phosphatase Gene," *J. Biol. Chem.* 269:3596-3604 (1994)). Consistent with these findings, loss of MKP-1 activity sensitizes neuronal cells to glutamate mediated toxicity and oxidative stress in vitro (Kim et al., "MKP-1 Contributes to Oxidative Stress-Induced Apoptosis Via Inactivation of ERK1/2 In SH-SY5Y Cells," *Biochem. Biophys. Res. Commun.* 338:1732-38 (2005); Choi et al., "Protein Kinase Cdelta-Mediated Proteasomal Degradation of MAP Kinase Phospohatase-1 Contributes to Glutamate-Induced Neuronal Cell Death," *J. Cell Sci.* 119:1329-40 (2006)). MKP-1 is induced after BDNF-mediated stimulation of the TrkB receptor (Glorioso et al., "Specificity and Timing of Neocortical Transcriptome Changes in Response to BDNF Gene Ablation During Embryogenesis or Adulthood," *Mol. Psychiatry* 11:633-48 (2006)).

The present invention overcomes limitations in the art by providing strategies aimed at modulating MKP-1's activity towards HIF, or directly regulating the machinery involved in HIF-1α cleavage, as therapeutic strategies for stroke and associated disorders in which ischemia is a central component.

SUMMARY OF THE INVENTION

One aspect of the present invention is directed to a method of treating a patient for a condition where blood flow to a tissue or organ is interrupted. This method involves administering to a patient with a hypoxic condition where blood flow to a tissue or organ is interrupted, or at risk thereof, a compound that reduces the rate of HIF-1α inactivation in cells affected by the condition, thereby treating the patient for the condition.

Another aspect of the present invention relates to a method of treating a tumor in a patient. This method involves administering to the patient a compound capable of altering activity of HIF-1α in tumor cells.

A further aspect of the present invention relates to a method of identifying compounds as candidate drugs for treatment of hypoxic conditions. This method involves providing a cell expressing HIF-1α, wherein HIF-1α is cleaved or undergoes site-directed cleavage or proteolysis in the cell, contacting the cell with compounds to be evaluated, and selecting compounds capable of reducing HIF-1α cleavage and/or proteolysis in the cell as candidate drugs for treatment of hypoxic conditions.

Another aspect of the present invention relates to a method of identifying compounds as candidate drugs for treating tumors in a subject. This method involves providing a cell expressing active HIF-1α comprising a cleavage site, contacting the cell with a compound to be evaluated, and selecting a compound that either hyper-stimulates or inactivates HIF-1α as a candidate drug for treating tumors in a subject.

Since MKP-1 regulates the post-translational modification of HIF-1α (Liu et al., "Suppression of the Dual-Specificity Phosphatase MKP-1 Enhances HIF-1 Transactivation and Increases Expression of EPO," *Biochem. Biophys. Res. Commun.* 312:780-86 (2003), which is hereby incorporated by reference in its entirety), it was hypothesized that MKP-1 promotes HIF-1α's apoptotic signaling behavior. Data obtained pursuant to the present invention indicates that in addition to altering the growth and cell death responses of cells exposed to hypoxia, MKP-1 catalyzed the combinatorial post-translational modification and cleavage of HIF-1α. The observed shift in HIF-1α target gene expression towards pro-apoptotic targets support the hypothesis that MKP-1 is directly involved in the transcriptional switching behavior of HIF-1α.

As described herein, hypoxia activates both adaptive and latent apoptotic transcriptional responses and influences neuron survival in a variety of stroke paradigms. This pathway involves sensing pathways originating in the ER and mitochondria culminating in the coordinated destruction of both nuclear and cytoplasmic compartments. The present invention provides a solution to this problem by determining that the dual specificity phosphatase DUSP1/MKP-1 is responsible for the proposed switching behavior of HIF-1α, thus promoting delayed cell death after hypoxia. The present invention, for the first time, identifies a novel low molecular weight ("LMW") form of HIF-1α induced by DUSP1 activity, whose expression correlates with the elaboration of multiple pro death markers.

BRIEF DESCRIPTION OF THE DRAWINGS

FIG. 1A is a fluorescence microscopy photograph showing doxycycline (Dox) regulated transgene induction in pBig2i stable HN33 lines. After double selection, stable lines expressing GFP alone (multiple cloning site ("MCS")), wild type (MKP1), or the catalytic mutant MKP-1 ("C.S.") were exposed to doxycycline (2 μg/ml, 24 h) and imaged by fluorescence microscopy (40×). FIG. 1B is a graph showing MKP1 expression restricting cell growth in normoxic HN33.11 cells. Cells were seeded at $3 \times 10^5$ in 60 mm dishes grown for 3 days in 10% stripped FCS. Replicate samples (n=5) were trypsinized and viable cells were scored using the trypan blue exclusion. FIG. 1C shows the results of a time course analysis of doxycycline regulated expression of MKP1-myc and MKP1cs-myc and IRES driven GFP expression in stable lines. Normoxic cultures were plated and Dox treated. Samples were harvested at the times indicated and analyzed for GFP, Myc-tagged MKP-wt or C.S., and cCasp3 expression. βIII-tubulin was used as a loading control. FIG. 1D shows that MKP1 expressing lines are more susceptible to hypoxic challenge based on cCasp3 levels.

FIG. 2A provides graphs showing that DUSP1/MKP-1 expression activates several markers of programmed cell death in hypoxic HN33 lines, including cPARP, and cCasp-3, -9, and -12. Stable lines as indicated were exposed to hypoxia (0.5% $O_2$) for between 0-16 hrs and analyzed for the above targets by western blotting. FIG. 2B is a schematic illustration of the various domains of MKP-1 protein and constructs used in the present invention. FIG. 2C is a Western blot showing that the CH2AB domain is sufficient to activate cCasp3 cleavage in acutely transfected hypoxic HN33 cells. Cells were transfected with the constructs as indicated and exposed to hypoxia for 24 hrs prior to Western analysis for cCasp3 and actin levels. GFP blotting designates the pertinent expression levels of the various fusion constructs. Non-specific bands are indicated (NS).

FIG. 3 further illustrates that MKP1 alters expression of HIF-1 targets bNIP3 and NOXA, but not hexokinase II (HkII) or p53. Stable lines were treated with doxycycline (2 mg/ml) overnight and exposed to hypoxia (0.5% $O_2$) for the time indicated. Whole cell lysates were collected and analyzed by Western blotting for the specified targets.

FIG. 4A is a schematic illustration of the chimeric myc-HIF-1α-V5 dual epitope tagged construct used to study MKP-1 mediated changes in combinatorial HIF-1α post-translational processing. FIG. 4B shows that MKP1 induces the generation of a low molecular weight HIF-1α species ("LMW-HIF") through post-translational modification. FIG. 4C illustrates that MKP1 induces the generation of a myc-HIF/V5 cleavage product detected using both myc and V5 anti-sera. FIG. 4D illustrates cycloheximide (CHX) pulse-chase and treatment with the proteosome inhibitor MG132 inducing several LMW-HIF-1α species in hypoxic HN33 lysates. Myc-HIF-V5 transfected HN33 lines were acutely treated with cycloheximide and lysates were prepared at the times indicated from normoxic monolayers and resolved by PAGE. Western blotting detected both the major, full-length HIF-1α species (single asterisk) as well as two lower molecular weight species of HIF-1α (double and triple asterisks).

FIG. 5A is a schematic illustration of the domain structure of HIF-1α and the amino- and carboxy-terminal antibodies used to study MKP-1 mediated generation of LMW-HIF-1α forms. FIG. 5B shows a Western analysis with the amino- and carboxy-terminal anti-sera detecting complementary HIF-sub fragments in hypoxic stable HN33.11 lines using internal (single asterisk) and c-terminal (double asterisk) antibodies. FIG. 5C illustrates MKP-1 activating HIF-1α cleavage in a serum dependent manner. FIG. 5D depicts HIF-1α cleavage occurring in a variety of cell types. It further illustrates an analysis of MKP-1, HIF-1α, and HIF-1 targets in the murine cell line N2A and the human neuroblastoma lines SKN and SHEP.

FIG. 7A shows results of mouse neuroblastoma cells that were transfected with empty vector (pUB6) or plasmid expressing the full length mouse cDNA encoding HIF-1α (mHIF) and incubated for 24 hrs under control conditions. Effects of MKP overexpression were tested by co-expressing either empty plasmid (pSG5) or vector expressing wildtype MKP-1 (pSG5-MKPwt; compare lanes 1 vs 2 & 3). Parallel samples were also treated with the proteosome inhibitor MG132 to determine whether sub fragments could be stabilized. Full-length and c-terminal fragments were identified using the carboxy-terminal V5 tag. FIG. 7B depicts optimization of expression conditions for human HIF-V5-6×His. Full-length and the proteolytic cleavage form of human HIF-1α are observed when expressed in the mouse N2A line. Other bands are shown as present in both samples and are cross reactive contaminants with V5 antibody. FIG. 7C illustrates affinity purification of the c-terminal HIF-1α fragment using the 6×His tag resin. N2A cells were transfected with the empty (pUB6-MCS) or HIF-expressing plasmids (pUb6-hHIF) and exposed to MG132 to induce fragment accumulation. Western blotting using the HIF-1α c-terminal antisera were used to demonstrate efficient purification of the HIF-1α cleavage species (lane 4) from several major contaminating species present in the crude lysates (lanes 1 and 2).

FIGS. 8A-B depict LCMS sequencing results of the HIF-1α carboxy terminal fragment. The full length peptide was subjected to mass spectrometry and results for tags identified were superimposed on the primary amino acid sequence for human HIF-1α (shown in bold letters). The peptides identified for the c-terminal fragment are shown in FIG. 8B (SEQ ID NO:5) with overlapping peptides as shown in bold letters. Thus, this data suggests the cleavage site exists upstream of the AA539 site identified in the C-terminal fragment and downstream of the last peptide sequence not-overlapping the C-terminal protein (i.e., NQEVALK (SEQ ID NO:6) at AA 471-477). FIG. 8A contains the peptides (in bold) that were identified after mass spectrometry using a polyacrylamide gel plug containing proteins running at the size of full length HIF-1α. This confirms that the protein of interest is detected from the background of other proteins in that size range. FIG. 8B is the same analysis only using the smaller range protein, which contains the C-terminal HIF-1α fragment. Thus, it can be inferred, based on the peptides mapped against the full length sequence, roughly what residues are contained in this peptide. Sequences upstream of the first bold block in FIG. 8B and downstream of the last unique peptide from FIG. 8A represent the location of the putative cleavage site.

DETAILED DESCRIPTION OF THE INVENTION

Figure 1:
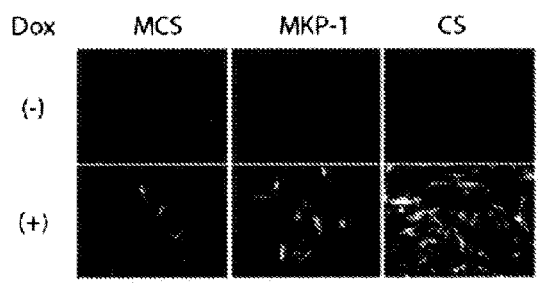
FIGS. 1A-D provide characterization data for inducible MKP-1 expression in HN33 cells.
Figure 1:
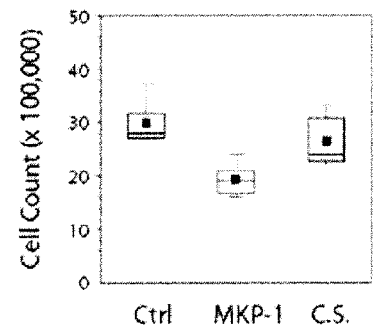
Figure 1:
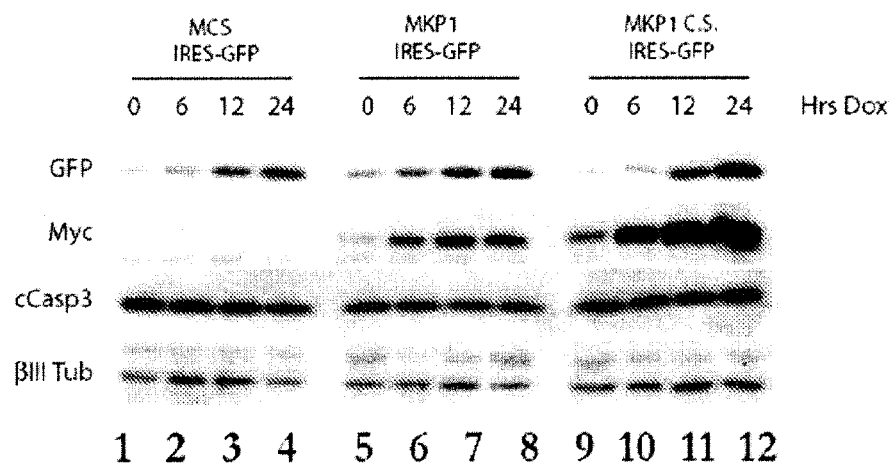
Figure 1:
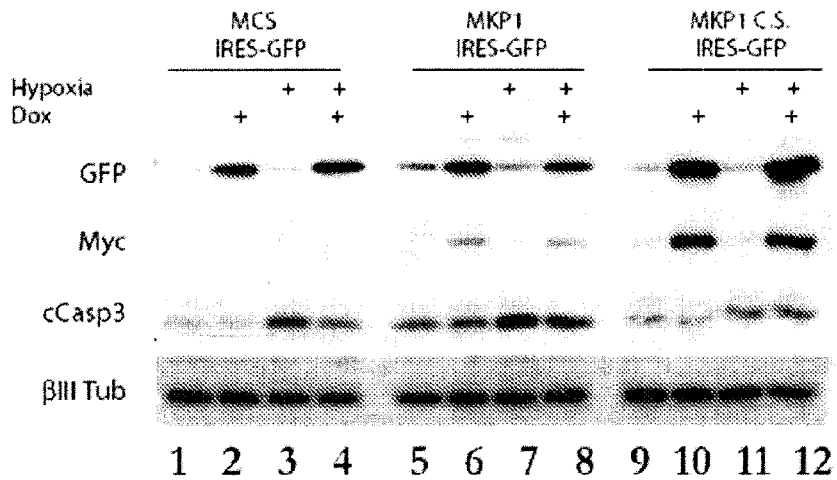

One aspect of the present invention relates to a method of treating a patient for a condition where blood flow to a tissue or organ is interrupted. Exemplary conditions include, but are not limited to, stroke, global ischemia after cardiac arrest, focal thrombotic and embolic large vessel stroke, small vessel stroke, asphyxiation, status epilepticus, carbon monoxide poisoning, fetal ischemic injury in utero for high risk pregnancy, systemic hypotension in shock, cardioprotection after acute coronary syndromes, or cerebral or systemic hypoxia sustained during e.g., bypass procedures. The method is carried out by administering to a patient with a hypoxic condition (e.g., one or more of the above conditions) where blood for to a tissue or organ is interrupted, or at risk thereof, a compound that reduces the rate of HIF-1α inactivation in cells affected by the condition, thereby treating the patient for the condition.

In one embodiment, the patient may be at risk for the hypoxic condition. A patient at risk may have, for example, a family history or personal history of susceptibility to hypoxic conditions. For example, the patient may have had a prior stroke or condition related thereto.

Compounds that are administered pursuant to this aspect of the invention may be targeted to alter cellular activity of MKP-1 in hypoxic cells (e.g., cells deficient in oxygen or at risk thereof). Altering cellular activity of MKP-1 may involve reducing cellular activity or increasing cellular activity of MKP-1. In one embodiment, MKP-1 activity is increased above the current level in a patient being treated, or a level that is above that of a normal, healthy human. In another embodiment, MKP-1 activity is decreased below the current level in a patient being treated, or a level that is below that of a normal, healthy human. Alternatively, the compounds may directly inhibit a cellular protease responsible for cleavage of HIF-1α.

In the method of treating a condition where blood flow to a tissue or organ is interrupted according to the present application, it may be desirable to administer compounds that inhibit MKP-1 activity Inhibitors of protein tyrosine phosphatases, such as MKP-1, are known in the art and include, without limitation, pentamidine; levamisole; ketoconazole; bisperoxovanadium compounds (e.g., those described in Scrivens et al., *Mol. Cancer. Ther.* 2:1053-59 (2003) and U.S. Pat. No. 6,642,221, which are hereby incorporated by reference in their entirety); vandate salts and complexes (e.g., sodium orthovanadate); dephosphatin; dnacin A1; dnacin A2; STI-571; suramin; gallium nitrate; sodium stibogluconate; meglumine antimonite; 2-(2-mercaptoethanol)-3-methyl-1, 4-naphthoquinone; 2,5-bis(4-amidinophenyl)furan-bis-O-methylamidoxime (known as DB289 (Immtech)); 2,5-bis(4-amidinophenyl)furan (DB75, Immtech), disclosed in U.S. Pat. No. 5,843,980, which is hereby incorporated by reference in its entirety; and compounds described in Pestell et al., *Oncogene* 19:6607-12 (2000); Lyon et al., *Nat. Rev. Drug Discov.* 1:961-76 (2002); Ducruet et al., *Bioorg. Med. Chem.* 8:1451-66 (2000); U.S. Patent Application Publication Nos. 2003/0114703, 2003/0144338, and 2003/0161893; and PCT Patent Publication Nos. WO99/46237, WO03/06788, and WO03/070158, all of which are hereby incorporated by reference in their entirety. Still other analogs are those that fall within a formula provided in any of U.S. Pat. Nos. 5,428,051; 5,521,189; 5,602,172; 5,643,935; 5,723,495; 5,843,980; 6,008,247; 6,025,398; 6,172,104; 6,214,883; and 6,326,395; U.S. Patent Application Publication Nos. 2001/0044468 and 2002/0019437; and the pentamidine analogs described in U.S. patent application Ser. No. 10/617,424 (see, e.g., Formula (II)), all of which are hereby incorporated by reference in their entirety. Other protein inhibitors can be identified, for example, using the methods described in Lazo et al., *Oncol. Res.* 13:347-52 (2003); PCT Publication Nos. WO97/40379, WO03/003001, and WO03/035621; and U.S. Pat. Nos. 5,443, 962 and 5,958,719, all of which are hereby incorporated by reference in their entirety.

Other inhibitors of MKP-1 can also be employed. Such inhibitors include compounds that reduce the amount of target protein or RNA levels (e.g., antisense compounds, dsRNA, ribozymes) and compounds that compete for binding partners (e.g., dominant negative proteins or polynucleotides encoding the same).

The biological activity of MKP-1 (or any other molecular target identified herein as amenable to treating a condition) can be reduced through the use of an antisense compound directed to RNA encoding the target protein. Antisense compounds against protein tyrosine phosphatases (e.g., MKP-1) may include, for example and without limitation, U.S. Patent Publication No. 2003/0083285 and Weil et al., *Biotechniques* 33:1244 (2002), which are hereby incorporated by reference in their entirety. Other antisense compounds that reduce MKP-1 activity can be identified using standard techniques. For example, accessible regions of MKP-1 mRNA can be predicted using an RNA secondary structure folding program such as MFOLD (M. Zuker, D. H. Mathews & D. H. Turner, Algorithms and Thermodynamics for RNA Secondary Structure Prediction: A Practical Guide. In: RNA Biochemistry and Biotechnology, J. Barciszewski & B. F. C. Clark, eds., NATO ASI Series, Kluwer Academic Publishers, (1999), which is hereby incorporated by reference in its entirety). Sub-optimal folds with a free energy value within 5% of the predicted most stable fold of the mRNA are predicted using a window of 200 bases within which a residue can find a complimentary base to form a base pair bond. Open regions that do not form a base pair are summed together with each sub-optimal fold and areas that are predicted as open are considered more accessible to the binding to antisense nucleobase oligomers. Other methods for antisense design are described, for example, in U.S. Pat. No. 6,472,521; *Antisense Nucleic Acid Drug Dev.* 1997 7:439-44; *Nucleic Acids Research* 28:2597-2604 (2000); and *Nucleic Acids Research* 31:4989-94 (2003), which are hereby incorporated by reference in their entirety.

The biological activity of MKP-1 (or any other drug target described herein) can be reduced through the use of RNA interference (RNAi), employing, e.g., a double stranded RNA (dsRNA) or small interfering RNA (siRNA) directed to the mitotic kinesin or protein tyrosine phosphatase in question (see, e.g., Miyamoto et al., *Prog. Cell Cycle Res.* 5:349-60 (2003); and U.S. Patent Application Publication. No. 2003/0157030, which are hereby incorporated by reference in their entirety). Methods for designing such interfering RNAs are known in the art. For example, software for designing interfering RNA is available from Oligoengine (Seattle, Wash.).

Compounds useful according to this aspect of the present invention may include compounds identified in screen assays described herein.

In yet a further embodiment, the method of treating a patient for a condition where blood flow to a tissue or organ is interrupted can be used for a patient who is at risk for the hypoxic condition.

In practicing the treatment methods of the present invention, the administering step is carried out by administering an agent (e.g., a compound that alters the rate of HIF-1α inactivation or cleavage) orally, intradermally, intramuscularly, intraperitoneally, intravenously, subcutaneously, or intranasally. The agent of the present invention may be administered alone or with suitable pharmaceutical carriers, and can be in solid or liquid form, such as tablets, capsules, powders, solutions, suspensions, or emulsions.

The agent may be orally administered, for example, with an inert diluent, or with an assimilable edible carrier, or it may be enclosed in hard or soft shell capsules, or it may be compressed into tablets, or it may be incorporated directly with food. For oral therapeutic administration, the agent of the present invention may be incorporated with excipients and used in the form of tablets, capsules, elixirs, suspensions, syrups, and the like. Such compositions and preparations should contain at least 0.1% of the agent. The percentage of the agent in these compositions may, of course, be varied and may conveniently be between about 2% to about 60% of the weight of the unit. The amount of agent in such therapeutically useful compositions is such that a suitable dosage will be obtained.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

Compounds may also be administered parenterally. Solutions or suspensions of the agent can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

Compounds may also be administered directly to the airways in the form of an aerosol. For use as aerosols, the agent of the present invention in solution or suspension may be packaged in a pressurized aerosol container together with suitable propellants, for example, hydrocarbon propellants like propane, butane, or isobutane with conventional adjuvants. Compounds may be administered in a non-pressurized form such as in a nebulizer or atomizer.

Suitable patients for this and other aspects of the present invention include, without limitation, any mammal, preferably a human.

Another aspect of the present invention is directed to a method of treating a tumor in a patient. This method involves administering to the patient a compound capable of disrupting activity of HIF-1α in tumor cells. In one embodiment, for example, the compound may further be capable of inactivating the protective activity of HIF-1α through activation of a putative proteolytic site and subsequent cleavage of HIF-1α by endogenous proteases. In another embodiment, the compound may upregulate activity of MKP-1 in tumor cells. In yet a further embodiment, the compound may alter HIF-1α specific modifications permitting site specific cleavage by cellular proteases.

Compounds useful according to this aspect of the present invention may include antisense compounds, such as those identified, for example, in U.S. Pat. No. 7,205,283 to Yoon et al., which is hereby incorporated by reference in its entirety. Other compounds and strategies for disrupting HIF-1α are disclosed in U.S. Pat. No. 7,521,431 to Reich et al., which is hereby incorporated by reference in its entirety. Compounds useful according to this aspect of the present invention may include compounds identified in screen assays described herein.

According to this method, compounds are administered to a subject with a tumor to treat disorders where aberrant angiogenesis is a central component, including cancer. The method may be employed to inhibit the further growth or spread of, e.g., malignant cells, and/or to cause dormancy or death of the malignant cells. Exemplary types of tumors that may be targeted include acute lymphocytic leukemia, acute myelogenous leukemia, biliary cancer, breast cancer, cervical cancer, chronic lymphocytic leukemia, chronic myelogenous leukemia, colorectal cancer, endometrial cancer, esophageal cancer, gastric cancer, head and neck cancers, Hodgkin's lymphoma, lung cancer, medullary thyroid cancer, non-Hodgkin's lymphoma, multiple myeloma, renal cancer, ovarian cancer, pancreatic cancer, melanoma, liver cancer, prostate cancer, glial and other brain and spinal cord tumors, and urinary bladder cancer.

This method may also be suitable for treating cancer. In particular, head and neck squamous cell carcinoma (HNSCC), breast cancer, ovarian cancer, prostate cancer, colon cancer, squamous carcinoma of the skin, glioblastoma, endometrial carcinoma, gastric cancer, pancreatic cancer, renal cell carcinoma, squamous cell lung cancer, and bladder cancer are amenable to the treatment in accordance with the method of the present invention. Treating cancer and inducing cancer cells into dormancy also encompasses treating a subject having premalignant conditions to stop the progression of, or cause regression of, the premalignant conditions. Examples of premalignant conditions include hyperplasia, dysplasia, and metaplasia.

Another aspect of the present invention is directed to methods of identifying compounds as candidate drugs for the treatment of hypoxic conditions. This method involves providing a cell expressing HIF-1α, where HIF-1α is cleaved or undergoes site-directed cleavage or proteolysis in the cell. The cell is contacted with a compound to be evaluated. Compounds are selected based on their ability to reduce HIF-1α cleavage and/or proteolysis in the cell.

In one embodiment, the cell may further express one or more of MKP-1, a protease known to cleave HIF-1α, and/or pro-apoptotic proteins. In another embodiment, compounds may be further selected based on their ability to down-regulate MKP-1 activity/expression in the cell. In an additional embodiment, the cell may further express pro-apoptotic proteins. In an additional embodiment, compounds may be further selected based on their ability to down-regulate activity of pro-apoptotic proteins (e.g., BNIP3, NOXA). In yet another embodiment, the cell may further express a protease known to cleave HIF-1α. Compounds may be further selected based on their ability to inhibit HIF-1α cleavage activity of a protease known to cleave HIF-1α that is also expressed in the cell.

Another aspect of the present invention involves a method of identifying compounds as candidate drugs for treating tumors in a subject. This method involves providing a cell expressing active HIF-1α comprising a cleavage site, contacting the cell with a compound to be evaluated, and selecting a compound that either hyper-stimulates or inactivates HIF-1α as a candidate drug for treating tumors in a subject.

In one embodiment, the cell expressing active HIF-1α may be subject to hypoxic conditions and a compound that inactivates HIF-1α is selected by detecting no increase or a decrease of active HIF-1α in the cell. In another embodiment, the compound may be selected based on an ability to cleave HIF-1α. In yet a further embodiment, cleavage of HIF-1α may be detected by detecting more than one HIF-1α fragment in the cell. In another embodiment, the HIF-1α cleavage produces two or more distinct fragments of HIF-1α. In yet a further embodiment, HIF-1α cleavage may be activated by MKP-1. The cell may also further express MKP-1 in an additional embodiment. In yet another embodiment, the compounds may further be selected based on their ability to upregulate MKP-1 activity/expression in the cell.

In carrying out the methods of identifying compounds, a cell is provided which expresses HIF-1α, including active HIF-1α comprising a cleavage site. The cell may also express, in addition to HIF-1α, MKP-1, a protease known to cleave HIF-1α, and/or pro-apoptotic proteins. To this end, a nucleic acid molecule encoding HIF-1α and, optionally, any other protein identified above (e.g., MKP-1, and/or pro-apoptotic proteins) can be introduced into an expression system of choice using conventional recombinant technology. Generally, this involves inserting the nucleic acid molecule into an expression system to which the molecule is heterologous (i.e., not normally present). The introduction of a particular foreign or native gene into a mammalian host is facilitated by first introducing the gene sequence into a suitable nucleic acid vector. "Vector" is used herein to mean any genetic element, such as a plasmid, phage, transposon, cosmid, chromosome, virus, virion, etc., which is capable of replication when associated with the proper control elements and which is capable of transferring gene sequences between cells. Thus, the term includes cloning and expression vectors, as well as viral vectors. The heterologous nucleic acid molecule is inserted into the expression system or vector in proper sense (5'→3') orientation and correct reading frame. The vector contains the necessary elements for the transcription and translation of the inserted HIF-1α-coding sequences.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Recombinant genes may also be introduced into viruses, including vaccinia virus, adenovirus, and retroviruses, including lentivirus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK+/− or KS+/− (see "Stratagene Cloning Systems" Catalog (1993) from Stratagene, La Jolla, Calif., which is hereby incorporated by reference in its entirety), pQE, pIH821, pGEX, pET series (see F. W. Studier et. al., "Use of T7 RNA Polymerase to Direct Expression of Cloned Genes," *Gene Expression Technology* Vol. 185 (1990), which is hereby incorporated by reference in its entirety), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Cold Springs Laboratory, Cold Springs Harbor, N.Y. (1989), which is hereby incorporated by reference in its entirety.

A variety of host-vector systems may be utilized to express HIF-1α-encoding sequence in a cell. Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA ("mRNA") translation).

Transcription of DNA is dependent upon the presence of a promoter which is a DNA sequence that directs the binding of RNA polymerase and thereby promotes mRNA synthesis. The DNA sequences of eukaryotic promoters differ from those of prokaryotic promoters. Furthermore, eukaryotic promoters and accompanying genetic signals may not be recognized in or may not function in a prokaryotic system, and, further, prokaryotic promoters are not recognized and do not function in eukaryotic cells.

Similarly, translation of mRNA in prokaryotes depends upon the presence of the proper prokaryotic signals which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression see Roberts and Lauer, *Methods in Enzymology*, 68:473 (1979), which is hereby incorporated by reference in its entirety.

Promoters vary in their "strength" (i.e., their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others including, but not limited to, lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires a Shine-Dalgarno sequence about 7-9 bases 5' to the initiation codon (ATG) to provide a ribosome binding site. Thus, any SD-ATG combination that can be utilized by host cell ribosomes may be employed. Such combinations include, but are not limited to, the SD-ATG combination from the cro gene or the N gene of coliphage lambda, or from the *E. coli* tryptophan E, D, C, B, or A genes. Additionally, any SD-ATG combination produced by recombinant DNA or other techniques involving incorporation of synthetic nucleotides may be used.

Depending on the vector system and host utilized, any number of suitable transcription and/or translation elements, including constitutive, inducible, and repressible promoters, as well as minimal 5' promoter elements may be used.

The HIF-1α-encoding nucleic acid, a promoter molecule of choice, a suitable 3' regulatory region, and if desired, a reporter gene, are incorporated into a vector-expression system of choice to prepare a nucleic acid construct using standard cloning procedures known in the art, such as described by Sambrook et al., *Molecular Cloning: A Laboratory Manual*, Third Edition, Cold Spring Harbor: Cold Spring Harbor Laboratory Press, New York (2001), which is hereby incorporated by reference in its entirety.

The nucleic acid molecule encoding HIF-1α is inserted into a vector in the sense (i.e., 5'→3') direction, such that the open reading frame is properly oriented for the expression of the encoded HIF-1α under the control of a promoter of choice. Single or multiple nucleic acids may be ligated into an appropriate vector in this way, under the control of a suitable promoter, to prepare a nucleic acid construct.

Once the isolated nucleic acid molecule encoding HIF-1α has been cloned into an expression system, it is ready to be incorporated into a host cell. Recombinant molecules can be introduced into cells via transformation, particularly transduction, conjugation, lipofection, protoplast fusion, mobilization, particle bombardment, or electroporation. The DNA sequences are cloned into the host cell using standard cloning procedures known in the art, as described by Sambrook et al., *Molecular Cloning: A Laboratory Manual*, Second Edition, Cold Springs Laboratory, Cold Springs Harbor, N.Y. (1989), which is hereby incorporated by reference in its entirety. Suitable hosts include, but are not limited to, bacteria, virus, yeast, fungi, mammalian cells, insect cells, plant cells, and the like.

Typically, an antibiotic or other compound useful for selective growth of the transformed cells only is added as a supplement to the media. The compound to be used will be dictated by the selectable marker element present in the plasmid with which the host cell was transformed. Suitable genes are those which confer resistance to gentamycin, G418, hygromycin, puromycin, streptomycin, spectinomycin, tetracycline, chloramphenicol, and the like. Similarly, "reporter genes," which encode enzymes providing for production of an identifiable compound, or other markers which indicate relevant information regarding the outcome of gene delivery, are suitable. For example, various luminescent or phosphorescent reporter genes are also appropriate, such that the presence of the heterologous gene may be ascertained visually.

In all aspects of the present invention "contacting a cell" can be carried out as desired, including, but not limited to, contacting cells in culture with compounds to be selected in a suitable growth medium. Alternatively, mice, rats or other mammals are injected with compounds to be selected.

It will be appreciated by a person of ordinary skill in the art that several cell-based screens for both inhibitors of MKP-1 activity and inhibition of the HIF-1α protease could be employed. Such methods may involve expression of any one of several reporters (e.g., green fluorescent protein, luciferase, b-galactosidase) engineered to contain in a nonessential region the HIF-1α cleavage site such that when said site is cleaved, enzyme activity is lost. Another strategy could be to utilize combinations of, e.g., green fluorescent protein that when linked to either side of the site are inactive and activate after cleavage and separation.

Methods of identifying compounds according to the present invention may involve the identification of drugs, RNA interference strategies, as well as the identification of synthetic peptide inhibitors of HIF-1α cleavage. Similar cell permeable peptides have been used successfully in animal models of stroke to block the activation of various cellular apoptotic enzymes Inhibitors would contain the site recognized by the cellular protease.

Other aspects of the present invention relate to treating subjects for other diseases or disorders associated with or linked to HIF-1α, its expression, and/or its cleavage. In one embodiment, a method is provided for treating a patient for pulmonary hypertension or diabetic retinopathy by administering to a patient with such a condition a compound that down-regulates over-activation of HIF-1α.

In another embodiment, a method is provided for treating a patient for non-hypoxic conditions such as rheumatoid arthritis by administering to a patient with such a condition a compound that down-regulates over activation of HIF-1α.

In yet another embodiment, loss of HIF-1α activity against the gen VEGF accelerates loss of motorneurons associated with ALS. Thus, a method is provided for treating a patient with MLS by administering to a patient with such a condition a compound that increases HIF-1α activity.

A further aspect of the present invention is directed to an isolated HIF-1α cleavage fragment. In one embodiment, the fragment is a result of a single HIF-1α cleavage event at amino acid 539, 538, 537, 536, 535, 534, 533, 532, 531, 530, 529, 528, 527, 526, 525, 524, 523, 522, 521, 520, 519, 518, 517, 516, or 515. Alternatively, the isolated HIF-1α fragment is a fragment from a single cleavage event at a site between AA500-515, AA475-500, AA450-475, AA425-450, AA400-425, AA375-400, AA350-375, AA325-350, or AA300-325, or AA477-539 of HIF-1α.

EXAMPLES

The following examples are provided to illustrate embodiments of the present invention but are by no means intended to limit its scope.

Example 1

Cell Culture and Stable Line Generation

The HN33.11 line was passaged in DMEM/HG/5% stripped serum (Innovative Research, Novi, Mich.) unless otherwise specified. HN33 cells were generated by crossing mouse hippocampal neurons with the immortalized N18TG2 line (Lee et al., "Neuronal Properties and Trophic Activities of Immortalized Hippocampal Cells From Embryonic and Young Adult Mice," *J. Neurosci.* 10:1779-87 (1990), which is hereby incorporated by reference in its entirety). These cells maintain neuronal properties and have been used elsewhere to study neuronal responses to hypoxic stress (Peinado-Ramon et al., "MAP Kinase Phosphatase-1 mRNA is Expressed In Embryonic Sympathetic Neurons and is Upregulated After NGF Stimulation," *Brain Res. Mol. Brain. Res.* 56:256-67 (1998); Jin et al., "Vascular Endothelial Growth Factor Rescues HN33 Neural Cells From Death Induced by Serum Withdrawal," *J. Mol. Neurosci.*, 14:197-203 (2000), which are hereby incorporated by reference in their entirety). DAOY, SHEP-1, and N2AB1 lines were obtained from the ATCC and maintained in the above base media. The pBig21 doxycycline inducible system was used to create DUSP1 inducible stable cell lines (Strathdee et al., "Efficient Control of Tetracycline-Responsive Gene Expression From an Autoregulated Bi-Directional Expression Vector," *Gene* 229:21-29 (1999), which is hereby incorporated by reference in its entirety). cDNAs encoding a c-terminal myc-tagged version of wild-type human DUSP1 and a catalytically inactive form harboring a serine for cysteine mutation (Cys$^{258}$→Ser) were obtained from Cold Spring Harbor Laboratory (Cold Spring Harbor, N.Y.) (Sun et al., "MKP-1 (3CH134), an Immediate Early Gene Product, is a Dual Specificity Phosphatase that Dephosphorylates MAP Kinase In Vivo," *Cell* 75:487-93 (1993), which is hereby incorporated by reference in its entirety).

HN33 lines transfected with pBig21-IRES-GFP, pBig2i-MKP1-WT-IRES-GFP, and pBig2i-C.S.-IRES-GFP using Lipofectamine 2000 (Invitrogen) were selected using 400 µg/ml hygromycin for 10 days. To study the population of stable clones, resistant cultures were purified by FACS sorting for the GFP-negative population and subsequently re-sorted following doxycycline (Sigma Aldrich, St. Louis, Mo.) exposure (2 µg/ml; 12 h). For routine passage, cells were incubated in base media containing stripped serum without doxycycline.

Example 2

Cell Growth Analysis

For cell growth assays, 300,000 cells were plated to 60 mm well plates and grown in 10% stripped serum in the absence of doxycycline while under selection pressure (200 µg/ml hygromycin) and standard growth conditions. Plates prepared serially (n=5) for each stable line were trypsinized three days after plating, and cell counts were obtained using standard hemocytometry.

Example 3

Western Blotting

Cell lysates were obtained by rinsing monolayers with ice-cold PBS×1 followed by the addition of RIPA buffer containing both protease and phosphatase inhibitor cocktails (Sigma-Aldrich, St. Louis, Mo.). Samples were boiled in Laemmeli buffer and electrophoresed under reducing conditions on polyacrylamide gels. Proteins were transferred to PVDF membranes and blocked in TBS-T (50 nM Tris-HCl, pH 8.0, 0.9% NaCl, and 0.1% Tween-20™) containing 5% non-fat dry milk for 1 h at room temperature. Antibodies used in this study included: NeuN (Chemicon, Temecula, Calif.; 1:500), GFP, HIF-1α (Novus Biologicals, NB-100-449 and NB-100-131, Littleton, Colo.), TUJ1 & MKP-1 (Santa Cruz Biologicals, San Diego, Calif.; 1:500) Caspase 9, cleaved caspase-3, -9, -12, and cleaved PARP (CST, Danvers, Mass.). Blots were exposed to HRP conjugated secondary antibodies (Santa Cruz Biologicals, CA) prior to chemiluminescent detection (Amersham). To resolve molecular weight changes in HIF-1α, crude lysates were run on 15% PAGE gels.

Example 4

Tagged HIF-1α Vector Construction and Pulse-Chase Analyses

The cDNA for mouse HIF-1α was generated by RT-PCR using total cDNA from HN33.11 cultures using Superscript III according to the manufacturer's instructions using the random hexamer method (Invitrogen, Carlsbad, Calif.). PCR was performed using forward (5'-AGACAACGCGGGCAC-CGATT-3' (SEQ ID NO:1)) and reverse (5'-TCAG-TTAACT-TGATCCAAAGCTCT-3' (SEQ ID NO:2)) primers as described (Chun et al., "A New HIF-1 Alpha Variant Induced by Zinc Ion Suppresses HIF-1-Mediated Hypoxic Responses," *J. Cell Sci.* 114:4051-61 (2001), which is hereby incorporated by reference in its entirety), and the cDNA was sub-cloned to pCDNA3.1 and sequenced in its entirety. This sequence was sub-cloned using high fidelity polymerase and both the forward primer (5'-GCGGGATCCA TGGAACAAAAACTCATCTCAGAAGAAGATCTGAGT-TCTGAACGTCGAAAA GAA-3' (SEQ ID NO:3)) containing a BamHI site followed by a Kozak consensus sequence and the Myc epitope tag and the reverse primer (5'-ggggcg-gccgcTAA CTTGATCCAAAGC TCTGAGTAATTCT-TCACCCTGCAGTAG-3' (SEQ ID NO:4)) containing the Not I site allowing in frame ligation with the V5-6×His tag in pUB6-V5-6×HIS (Invitrogen). The mouse sequence for HIF-1α (Genbank accession NM_010431) was used to confirm primer specificity and cDNA sequences. Transfection grade DNA was prepared using the BioRad silica based Quantum prep method (Biorad, Temecula, Calif.).

Example 5

Analysis of Dox Inducible HN33.11 Lines Expressing MKP-1/DUSP1

Since DUSP1 inhibits HIF-1 transcriptional activity, it was hypothesized that the phosphatase would potentiate cellular toxicity in the setting of hypoxic stress. To test this, a set of stable cell lines was established containing a stably integrated doxycycline-inducible cassette containing wild-type MKP-1, a catalytic MKP-1 mutant (C.S.) or clones harboring only the multiple cloning sequence (MCS) upstream of the IRES-GFP cassette. In addition to mitigating the effects of either positive or negative selective pressure, this configuration provided a convenient way to track the kinetics of ligand regulated transgene expression (Strathdee et al., "Efficient Control of Tetracycline-Responsive Gene Expression From an Autoregulated Bi-Directional Expression Vector," *Gene* 229:21-29 (1999), which is hereby incorporated by reference in its entirety). Fluorescence microscopy confirmed robust Dox-inducible transgene expression in each of the three lines (FIG. 1A). Consistent with MKP-1's ability to limit progression through S-phase (Brondello et al., "Constitutive MAP Kinase Phosphatase (MKP-1) Expression Blocks G1 Specific Gene Transcription and S-Phase Entry in Fibroblasts," *Oncogene* 10:1895-1904 (1995), which is hereby incorporated by reference in its entirety), wild-type MKP-1 lines exhibited slower rates of cell division ($1.92 \times 10^6 \pm 0.31$) compared to either control ($2.98 \pm 0.42$ e6, $p=<0.0001$) or the C.S. line ($2.64 \times 10^6 \pm 0.48$, $p<0.002$; FIG. 1B). Further analysis indicated that MKP-1's effects on growth rate under normoxic conditions did not stem from increased levels of apoptotic cell death based on the observed stability in cleaved caspase-3 levels. All lines exhibited basal expression of the transgene in the absence of doxycycline treatment, a feature previously reported with the single plasmid tet-regulated system (FIG. 1C, wb: myc, lanes 1, 5 and 9). Exposure to doxycycline (2 µg/ml) stimulated transgene expression within 6 h (FIG. 1C). While MKP-1 C.S. levels increased up to 24 hr, wild-type MKP1 levels peaked within 12 hrs. The fact that MKP-1 expression was non-toxic under normoxic conditions (FIG. 1C; compare cCasp3 for lanes 1, 5 and 9), further suggests that MKP-1 might auto-regulate through a negative feedback mechanism.

Figure 2:
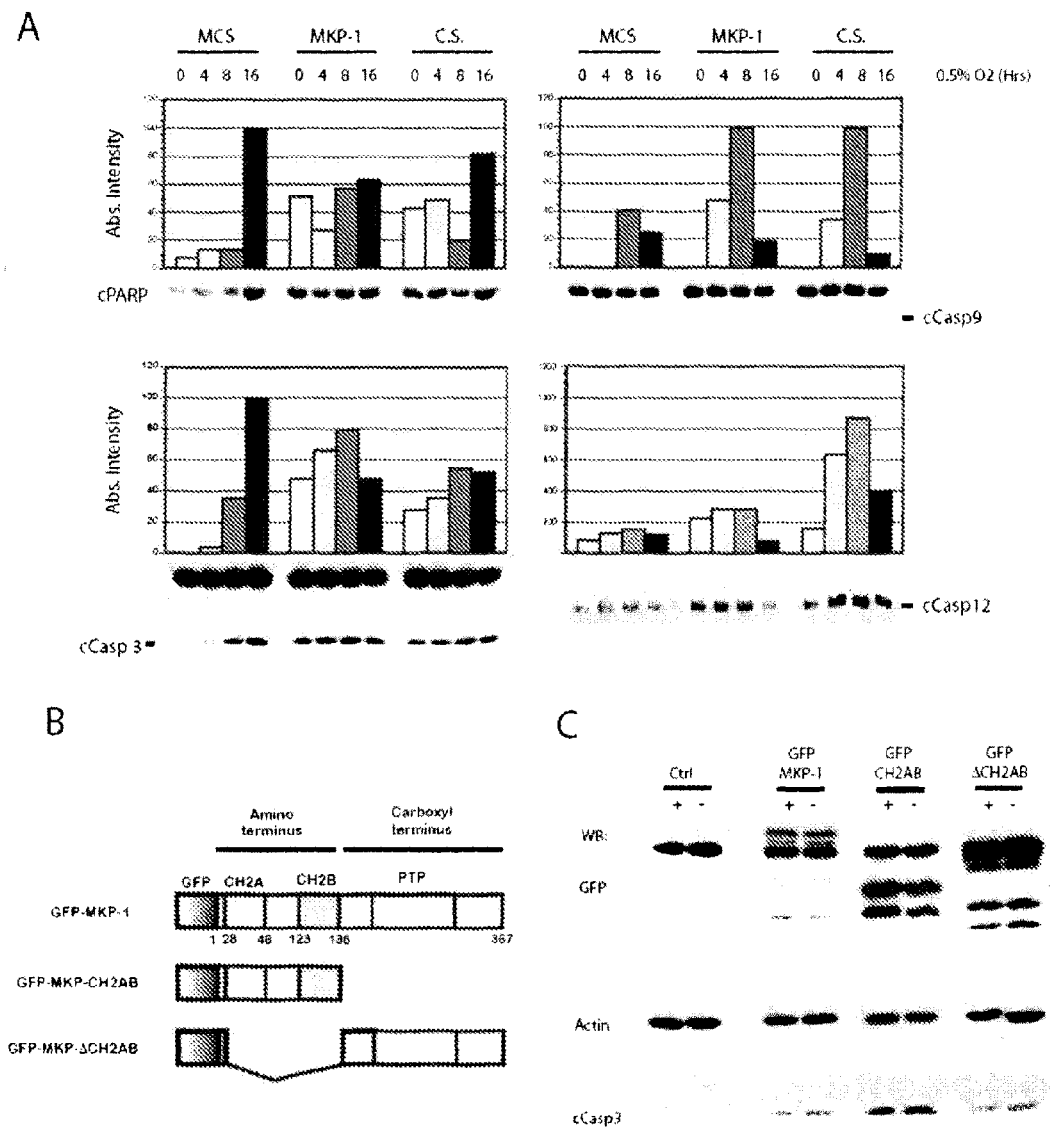
FIGS. 2A-C illustrate that MKP-1 sensitizes HN33.11 cells to hypoxia-induced apoptosis.

To determine whether MKP-1 expression sensitized cells to hypoxia-mediated injury, the effects of transgene expression on the activation of the apoptotic marker caspase-3 were tested. Hypoxia induced casp-3 cleavage in the control MCS line (FIG. 1D, lane 1 vs. 3). The ability to assess the effects of MKP-1 induction on cCasp3 cleavage was hindered by the observation that doxycycline alone provided partial protection (lane 3 vs. 4) as reported previously (Jantzie et al., "Doxycylcine Reduces Cleaved Caspase-3 and Microglial Activation In an Animal Model of Neonatal Hypoxia-Ischemia," *J. Cereb. Blood Flow Metab.* 25:314-34 (2005), which is hereby incorporated by reference in its entirety). Despite this effect, cCasp-3 levels were higher basally (lane 5 vs. 1), as well as following hypoxic treatment (lane 7 vs. 3) in wild-type DUSP1 stables. Interestingly, expression of the C.S. mutant induced near control levels of casp-3 cleavage (lane 3 vs. 11). To see whether this effect was generalizable, it was examined whether similar effects were true for other apoptotic markers. As shown in FIG. 2A, this appeared to be the case as stable cells expressing wild-type MKP-1 exhibited higher levels of PARP, casp-3, -9, and -12 overall. Similar trends were observed for the C.S. catalytic mutant, suggesting accessory domains outside the PTP catalytic region may be important in this facet of DUSP1 activity. The amino-terminus of MKP-1 contains two cdc25 homology domains (CH2A and CH2B; FIG. 2B) that participate in MKP-1's nuclear targeting and inhibition of MAPK-dependent phosphorylation through competition for MAPK substrates (Wu et al., "The Noncatalytic Amino Terminus of Mitogen-Activated Protein Kinase Phosphatase 1 Directs Clear Targeting and Serum Response Element Transcriptional Regulation," *Mol. Cell. Biol.* 25:4792-4803 (2005), which is hereby incorporated by reference in its entirety). To test whether the CH2 domains influenced caspase-3 cleavage, the effects of GFP fusion constructs co-expressing either wild-type MKP, the CH2 domains in isolation, or the MKP-1 open reading frame lacking the CH2AB region (GFPαCH2AB) in transiently transfected HN33.11 cells exposed to hypoxia were compared. The expected sizes and comparable levels of expression were observed for the fusion products (FIG. 2C, GFP). Compared to cCasp3 levels in the wild type MKP-1 GFP fusion, expression of the CH2AB domain was sufficient to enhance cCasp-3 levels not seen in the GFPαCH2AB transfected samples.

Example 6

Figure 3:
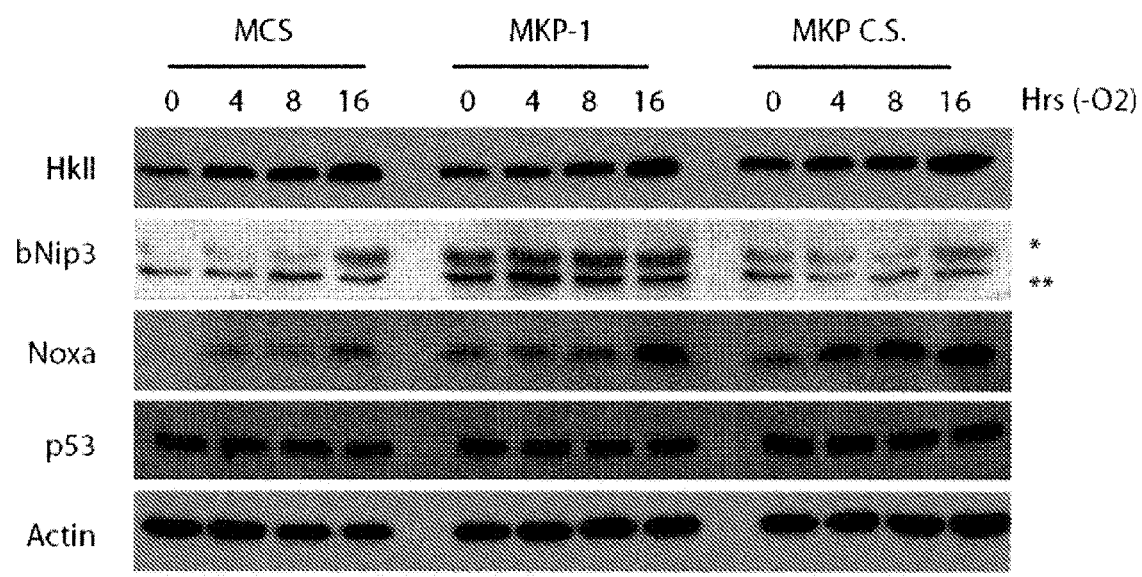
FIG. 3 is a Western blot showing that activation of MKP1 alters the target specificity of HIF-1 after hypoxic induction.

MKP-1 Expression Alters the Expression of Hypoxia-Regulated Transcriptional Targets To determine the upstream signaling events involved in MKP-1-sensitization of hypoxia-induced activation of the apoptosome, whether MKP-1 expression also influenced the expression HIF-1 targets linked with survival and apoptotic signaling in other systems was tested. In addition to its role in the glycolysis, the HIF-1α target hexokinase-II (HkII) exerts an anti-apoptotic influence on cells by stabilizing mitochondrial bioenergetics through direct interactions with mitochondrial proteins (Majewski et al., "Hexokinase-Mitochondria Interaction Mediated by Akt is Required to Inhibit Apoptosis in the Presence or Absence of Bax and Bak," *Mol. Cell.* 16:819-30 (2004), which is hereby incorporated by reference in its entirety). MKP-1 had no apparent activity on this transcriptional target (FIG. 3). However, MKP-1 stimulated expression of the pro-apoptotic HIF-1α targets bNip3 and Noxa, while leaving levels of p53 unchanged (FIG. 3) (Bruick, "Expression of the Gene Encoding the Proapoptic Nip3 Protein is Induced by Hypoxia," *Proc. Nat'l Acad. Sci.* 97:9082-87 (2000); Oda et al., "Noxa, a BH3-Only Member of the Bcl-2 Family and Candidate Mediator of p53-Induced Apoptosis," *Science* 288:1053-58 (2000); Kim et al., "BH3-Only Protein Noxa is a Mediator of Hypoxic Cell Death Induced by Hypoxia-Inducible Factor 1alpha," *J. Exp. Med.* 199:113-24 (2004), which are hereby incorporated by reference in their entirety). These data strongly suggest that MKP-mediated effects on HIF-1α's transcriptional activity might account for the observed activation of apoptotic markers in the model.

Example 7

MKP-1 Expression Alters the Stability of HIF-1α in HN33.11 Lines

Figure 4:
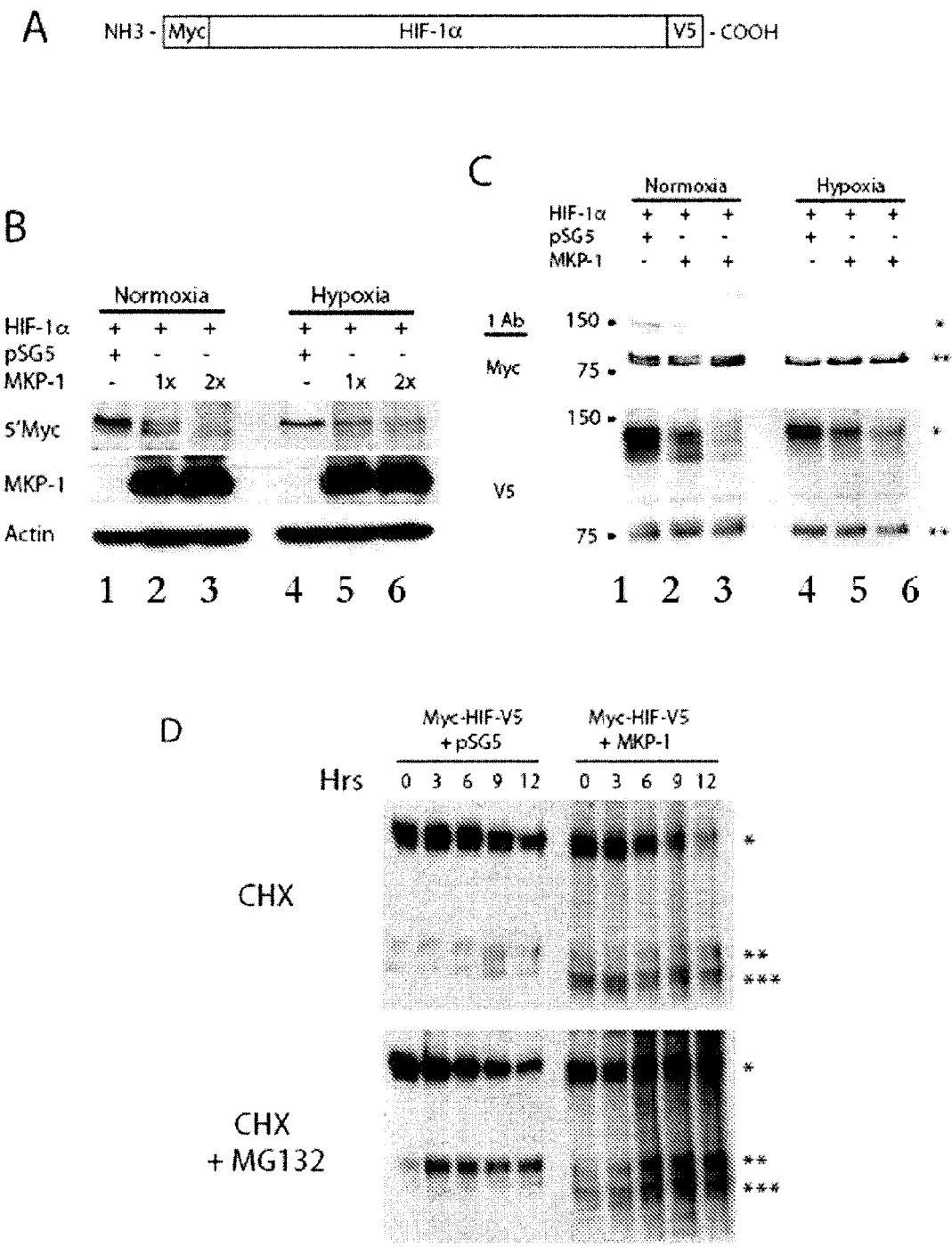
FIGS. 4A-D show that MKP-1 enables the site-specific cleavage of exogenously delivered HIF-1α.

After hypoxic stabilization, HIF-1α is subject to a complex array of potential post-translational modifications and migrates as a complex of bands between 110-130 kDa. Evidence indicates that MKP-1 modulates hypoxia-dependent transcription by catalyzing the removal of key regulatory phospho-epitopes from HIF-1α (Suzuki et al., "Dephosphorylated Hypoxia-Inducible Factor 1alpha as a Mediator of p53-Dependent Apoptosis During Hypoxia," *Oncogene* 20:5779-88 (2001), which is hereby incorporated by reference in its entirety). To screen for this activity in the tested model, a HIF-1α expression construct containing amino- (Myc) and carboxy-terminal (V5) epitope tags was constructed (FIG. 4A). Myc-HIF-V5 was then co-transfected with either empty vector (pSG5) or two doses of a Myc-tagged MKP-1 vector into HN33 cells and maintained under either normoxic or hypoxic conditions. In hypoxic, control samples the predominant Myc-HIF-V5 species ran at approximately 145 kDa consistent with the expected size of the chimeric protein (FIG. 4B, lane 1) also detected using the V5 anti-sera (FIG. 4C, lane 1). Addition of increasing amounts MKP-1 destabilized HIF-1α levels overall and reduced its apparent molecular weight (FIG. 4C, lane 2 vs. 3). Interestingly, while hypoxia did not reverse MKP-1's destabilizing effects on HIF, the relative molecular weight shift was impeded (FIG. 4C, lanes 5 & 6 vs. lane 4).

Example 8

DUSP1/MKP-1 Induces Internal Cleavage of HIF-1α

In the course of these investigations it was also noted that in addition to the expected full-length HIF-1α products, delivery of the myc-HIF-V5 construct also resulted in the expression of several smaller tagged-HIF-1α species (75-85 kDa; FIG. 4C, double asterisks). To study the relative stability of these various forms of the tagged HIF-1α species, pulse chase analyses were performed in which cells under normoxic conditions were transfected with the dual-tagged vector and allowed to express the product before addition of the translation inhibitor cycloheximide (2 μg/ml). Results indicate that in addition to destabilizing full-length HIF-1α, MKP-1 stimulated the formation two low weight HIF-1α sub-fragments (FIG. 4D, double and triple asterisk). Also, addition of the proteosome inhibitor MG132 appeared to negate the destabilizing effect of MKP-1 and enhanced the accumulation of the intermediate myc-HIF-V5 species independent of MKP-1 levels (FIG. 4D, double asterisk). These data indicate that in addition to destabilizing HIF-1α at the protein level, MKP-1 controls the ability of HN33 cells to generate several discrete and unstable HIF-1α cleavage products.

Figure 5:
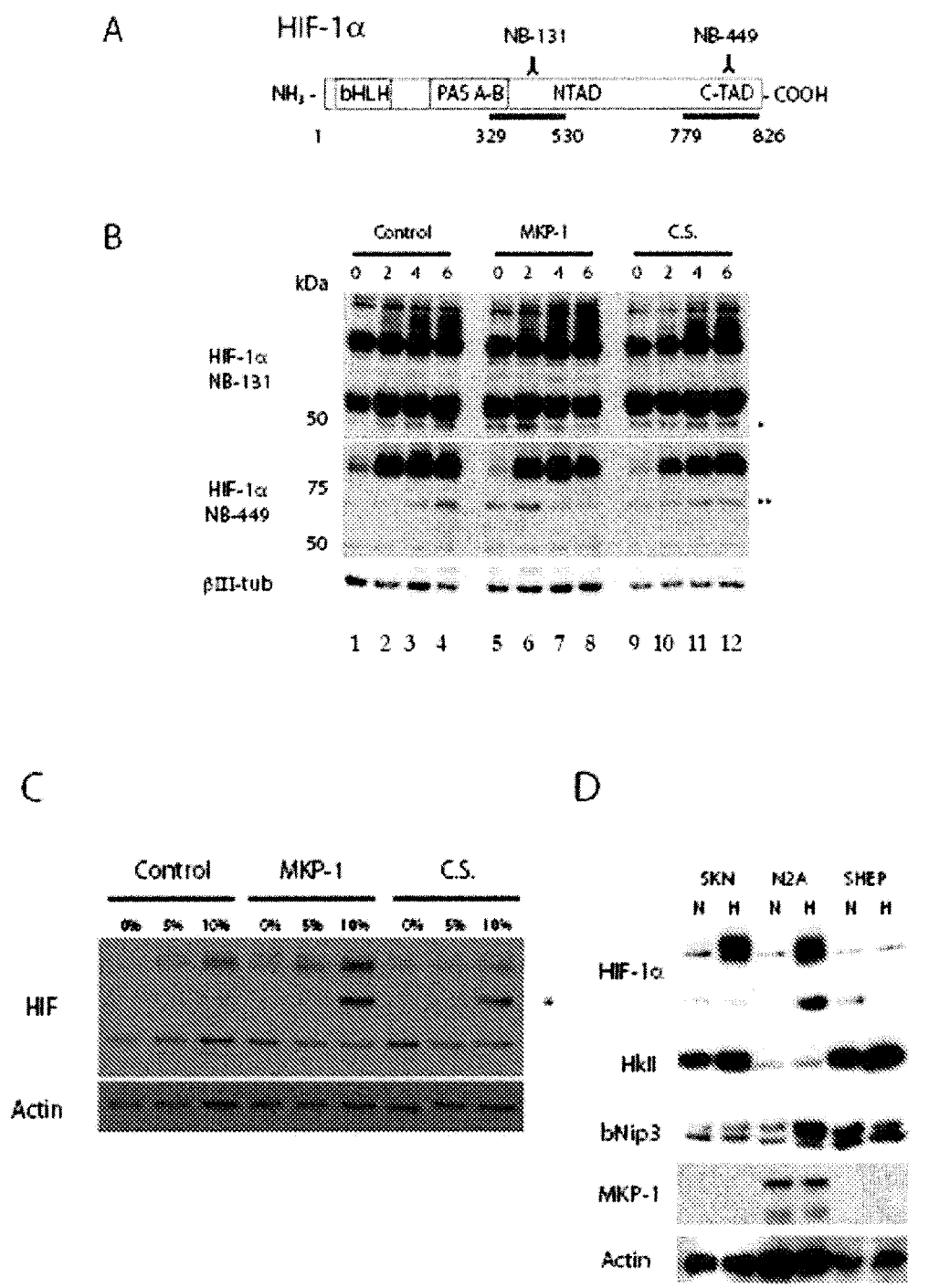
FIGS. 5A-D illustrate MKP-1 inducing cleavage of endogenous HIF-1α.

To confirm these effects were not an artifact of HIF-1α chimera over expression, the expression of endogenous sub-HIF-1α fragments using lysates from control and hypoxia-exposed MCS, MKP-1 wt, and C.S. cultures were screened. FIG. 5A illustrates the domain structure of HIF-1α and the antibodies used to characterize the relative levels of full length and the split N- and C-terminal HIF-1α products.

Results showed detectable comparable HIF-1α sub-fragments using HIF-1α amino-(single asterisk) and carboxy-terminal (double asterisk) specific antibodies (FIG. 5B). Interestingly, the aggregate molecular weight of these species (50 kDa & 70 kDa) approximates the approximate weight expected for endogenous, untagged HIF-1α (120 kDa; FIG. 5B, lanes 5-8 vs. 1-4). Again, these results are consistent with the model whereby HIF-1α is targeted by one or more endogenous cellular proteases.

In addition to its robust stabilization under hypoxic conditions, HIF-1α can also be stabilized in normoxic cells via growth factor-mediated tyrosine kinase receptor signaling. Interestingly, both full-length and LMW-HIF-1α levels of serum were responsive in the HN33.11 stables under normoxic conditions (FIG. 5C). This effect was most dramatic in the wild type MKP-1 line but present in both the C.S., and control MCS stable cell lines. Lastly, to determine if MKP-1 effects on HIF-1α cleavage was a generalizable phenomenon affecting other cell lines and species, the expression of HIF-1α, MKP-1 and the HIF-1 targets HkII and bNip3 in other cell types were studied. As shown, the human neuroblastoma cell lines SKN-AS and SHEP, as well the mouse neuronal line N2AB1 all expressed the lesser HIF-1α form (FIG. 5D). High-levels of endogenous MKP-1 expression was associated with the formation of LMW-HIF-1α species, the inhibition of HkII expression and elevated bNip3 levels. Conversely, lower levels of LMW-HIF-1α correlated with preserved induction of HkII and loss of Bnip3 regulation.

HIF-1α's transcriptional potency is subject to regulation through post-translational modification of both amino (N-TAD) and carboxy-terminal (C-TAD) segments of its transactivation domain (Richard et al., "p42/p44 Mitogen-Activated Protein Kinases Phosphorylate Hypoxia-Inducible Factor 1 alpha (HIF-1alpha) and Enhance Transcriptional Activity of HIF-1," *J. Biol. Chem.* 274:32631-37 (1999); Sodhi et al., "MAPK and Akt Act Cooperatively but Independently on Hypoxia Inducible Factor-1alpha in rasV12 Upregulation of VEGF,"*Biochem. Biophys. Res. Commun.* 287:292-300 (2001); Lee et al., "Two Transactivation Domains of Hypoxia-Inducible Factor-1alpha Regulated by the MEK-1/p42/p44 MAPK Pathway," *Mol. Cells.* 14:9-15 (2002); Ruas et al., "Functional Analysis of Hypoxia-Inducible Factor-1alpha-Mediated Transactivation. Identification of Amino Acid Residues Critical for Transcriptional Activation and/or Interaction with CREB-Binding Protein," *J. Biol. Chem.* 277:38723-30 (2002); Sang et al., "MAPK Signaling Up-Regulates the Activity of Hypoxia-Inducible Factors by its Effects on p300," *J. Biol. Chem.* 278:14013-19 (2003); Hu et al., "The N-Terminal Transactivation Domain Confers Target Gene Specificity of Hypoxia-Inducible Factors HIF-1 alpha and HIF-2alpha," *Mol. Biol. Cell* 18:4528-42 (2007); Lisy, "Turn Me On: Regulating HIF-1α Transcriptional Activity," *Cell Death Differ.* 15:642-49 (2008), which are hereby incorporated by reference in their entirety). The mitogen activated phosphokinase (MAPK) signaling pathway is involved in HIF-1α regulation (Wang et al., "Effect of Protein Kinase and Phosphatase Inhibitors on Expression of Hypoxia-Inducible Factor 1," *Biochem. Biophys. Res. Commun.* 216:669-75 (1995), which is hereby incorporated by reference in its entirety), and is activated by receptor-mediated signaling as well as through cell intrinsic pathways involving oxidative state of the cell among others. Not surprising, MAPK pathways are critical to cellular processes such as cell growth, differentiation, and apoptosis (Chang, "Mammalian MAP Kinase Signaling Cascades," *Nature* 410: 37-40 (2001), which is hereby incorporated by reference in its entirety). Conversely, the family of dual activity phosphatases (DUSPs) responsible for removing phosphates from tyrosine and threonine residues counteract MAPK signaling acting as a negative feedback pathway silencing these pro-stimulatory effects (Sun et al., "MKP-1 (3CH134), an Immediate Early Gene Product, Is a Dual Specificity Phosphatase that Dephosphorylates MAP Kinase In Vivo," *Cell* 75:487-93 (1993); Charles et al., "The Growth Factor-Inducible Immediate Early Gene 3CH134 Encodes a Protein-Tyrosine-Phosphatase," *Proc. Nat'l Acad. Sci.* 90:5292-96 (1993); Owens et al., "Differential Reuglation of MAP Kinase Signaling by Dual-Specificity Protein Phosphatases," *Oncogene* 26:3203-3213 (2007); Keyse, "Dual-Specificity MAP Kinase Phosphatases (MKPs) and Cancer," *Cancer Metastasis Rev.* 27:253-61 (2008), which are hereby incorporated by reference in their entirety).

Post-translational modification is also known to be important in regulating HIF's stability. This is dominated largely through the hydroxylation of HIF-1α catalyzed by the prolyl hydroxlyases that target prolyl (AA402 & AA564) and asparagine (AA803) residues respectively, which are amino acids on HIF-1α that are modified by hydroxylation and alter protein stability and transcriptional activity. These sites were not mutated directly, however, if AA564 is removed after C-terminal cleavage, it could alter protein stability and/or activity of the N-TAD. Acetylation at K532 also regulates stability by regulating VHL-mediated ubiquitination and proteolysis of HIF-1α protein. Phosphorylation by factors such as MAPK (specifically p42/p44) are linked with the regulation of HIF-1α's transcriptional activity, and modification of Thr796 has also been linked with binding partner specificity (Suzuki et al., "Dephosphorylated Hypoxia-Inducible Factor 1alpha as a Mediator of p53-Dependent Apoptosis During Hypoxia," *Oncogene* 20:5779-88 (2001) and Sodhi et al., "MAPK and Akt Act Cooperatively but Independently on Hypoxia Inducible Factor-1alpha In rasV12 Upregulation of VEGF,"*Biochem. Biophys. Res. Commun.* 287:292-300 (2001), which are hereby incorporated by reference in their entirety). Richard et al., "p42/p44 Mitogen-Activated Protein Kinases Phosphorylate Hypoxia-Inducible Factor 1 alpha (HIF-1alpha) and Enhance Transcriptional Activity of HIF-1," *J. Biol. Chem.* 274:32631-37 (1999), which is hereby incorporated by reference in its entirety, demonstrated that treatment with lambda phosphatase reduced the complex doublet to a single 103 kDa and effect mimicked by the application of the MEK inhibitor PD98059. Sodhi et al., "MAPK and Akt Act Cooperatively But Independently on Hypoxia Inducible Factor-1alpha In rasV12 Upregulation of VEGF," *Biochem. Biophys. Res. Commun.* 287:292-300 (2001), which is hereby incorporated by reference in its entirety, showed that both MAPK and p38a, but not JNK, could phosphorylate HIF's TAD (AA531-826). However, phosphorylation has not been thought to influence either the stability or DNA binding activity of HIF1α (Richard et al., "p42/p44 Mitogen-Activated Protein Kinases Phosphorylate Hypoxia-Inducible Factor 1 alpha (HIF-1alpha) and Enhance Transcriptional Activity of HIF-1," *J. Biol. Chem.* 274:32631-37 (1999), which is hereby incorporated by reference in its entirety). The data suggests this in fact is untrue, and implicate MKP-1 in HIF-1α stability presumably through its effects on HIF's phosphorylation status.

Results from Baranova et al., "Neuron-Specific Inactivation of the Hypoxia Inducible Factor 1 Alpha Increases Brain Injury In a Mouse Model of Transient Focal Cerebral Ischemia," *J. Neurosci.* 27:6320-32 (2007), which is hereby incorporated by reference in its entirety, suggest that stabilization of HIF-1α alone is insufficient to activate latent apoptotic signaling after ischemic stress. Under basal conditions MKP-1 appears to be expressed in areas of the adult mouse brain that are particularly sensitive to hypoxic injury including the hippocampus and cortex, and as an immediate early gene it is expressed early after ischemia in the central nervous system (Heintz, "Gene Expression Nervous System Atlas (GENSAT)," *Nat. Neurosci.* 7:483 (2004), which is hereby incorporated by reference in its entirety). In the CNS, MKP-1 is under the control of E Box promoter and responds to the PAS proteins Bmal and Clock protein linking it to the regulation of circadian rhythms. MKP-1's transcriptional activity is also regulated by ligand-receptor interactions on the cell surface. These include VEGF mediated signaling through the VEGF-2R receptor, by thrombin activation of its cognate receptors, and by activation of the neuropillin receptor by the soluble HIF-1 induced factor adrenomedulin. MKP-1 is also a transcriptional target of p53. Consequently, cells deficient in p53 activity exhibit higher levels of HIF-1 mediated transcriptional target induction, consistent with reports the MKP-1 acts as a negative feed back mechanism to limit excessive HIF-mediated pro-survival signaling.

Figure 6:
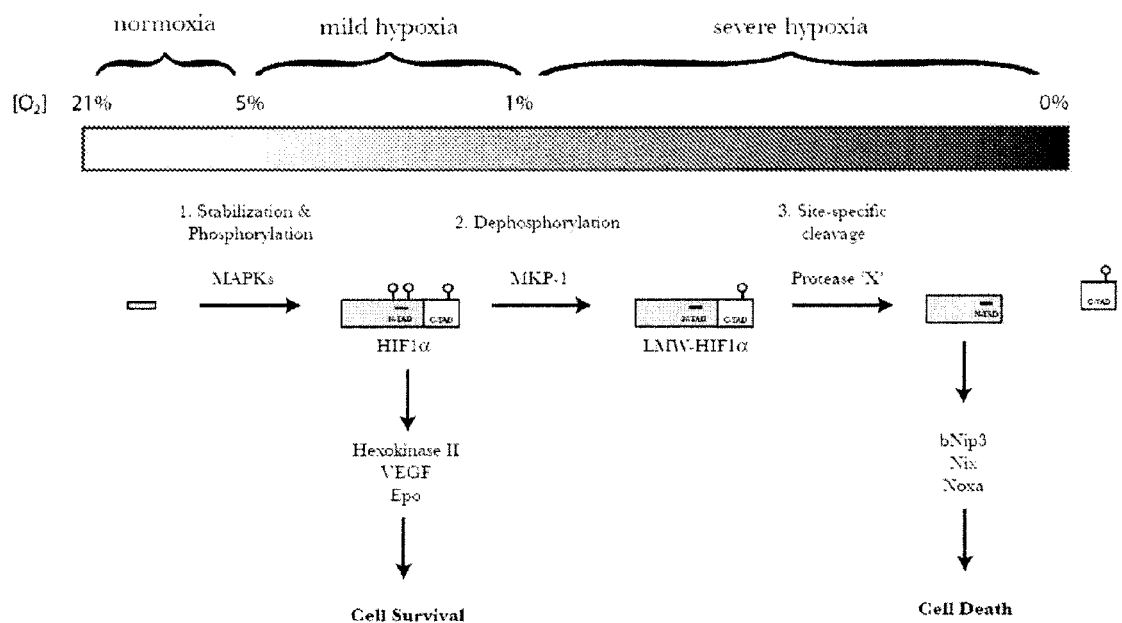
FIG. 6 is a schematic illustration depicting a proposed mechanism of MKP-1 mediated regulation of HIF-1α proteolytic processing. In the model presented, hypoxia inactivation of the prolyl hydroxylases allows HIF-1α to escape from ubiquitin-mediated degradation. The stable pool of HIF-1α is then activated by MAPK dependent phosphorylation resulting in activated C-terminal transactivation domain ("C-TAD") and other regulatory domains. In the second stage, activation of MKP-1 results in HIF-1α dephosphorylation, formation of a faster migrating HIF-1α species, which may exhibit differences in terms of protein-protein interactions. In the third stage, unmasking of a latent proteolytic cleavage site by MKP-1 allows LMW-HIF-1α to be targeted by endogenous cellular proteases at one or several sites downstream of the centrally located accessory N-terminal transactivation domain ("N-TAD"). Release of the C-TAD and activation of the N-TAD culminates in the expression of HIF-dependent pro-apoptotic signaling intermediates, including bNip3.

The data suggests that MKP-1 may participate in a novel pathway designed to inactivate HIF-1α-mediated adaptive signaling through the site-specific cleavage of HIF-1α (FIG. 6). Under mild conditions of hypoxia, inhibition of prolyl-hydroxylases results in the accumulation of HIF-1α protein. Activation of second messenger signaling pathways and subsequent activation of the transcriptional activation domain (TAD) results in the expression of a variety of adaptive gene targets including hexokinase II (HkII), the vascular endothelial growth factor (VEGF) and others. With more extreme hypoxia and increases in reactive oxygen species the dual activity phosphatase MKP-1 is induced catalyzing the removal of phosphate groups from, and inducing the molecular weight shift of HIF. This modification appears important in activating HIF-1α proteolysis resulting in the generation of complementary amino- and carboxyl-terminal HIF-1α fragments (FIG. 6, Step 3). While LMW-HIF-1α stabilization and subsequent association with p53 may transactivate the HIF-1α and p53 sites present in both Noxa and PUMA promoters, an increase in p53 expression was not observed in the system suggesting that HIF-mediated death signaling occurs through a distinct pathway.

While the formation of the LMW-HIF-1α species has been reported previously, a novel set of HIF-1 related fragments were identified whose expression exhibits a dependence on MKP-1 activity. The current model suggests that MKP-1 catalyzes the removal of key regulatory phosphates from an internal domain of HIF-1α that under mild-hypoxia mask a proteolytic cleavage site. Protection of this site supports retention of the C-TAD and transactivation of many adaptive transcriptional targets. With increasing levels of hypoxia and activation of MKP-1, these sites are removed and cellular proteases mediated the cleavage and removal of the C-TAD exposing an internal N-TAD which has been linked with the preferential activation of apoptotic transcripts including bNip3. This scenario thus suggests a number of potential genetic and pharmacological treatments that could alter HIF-1 dependent transcription in diseases such as stroke and cancer. For example, identification and inhibition of either MKP-1 activity or the cellular protease responsible for cleaving HIF-1α would be expected to confer cytoprotection under extreme hypoxia. Conversely, activation of MKP-1 activity or direct activation of the HIF-1α cellular protease would be expected to convert HIF-1α to its pro-death form, which could be used to target resistant tumor cell populations residing within hypoxic regions of a wide variety of tumor types.

Figure 7:
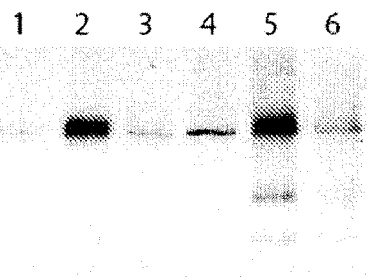
FIGS. 7A-C illustrate in vitro characterization and purification of HIF-1α cleavage product.
Figure 7:
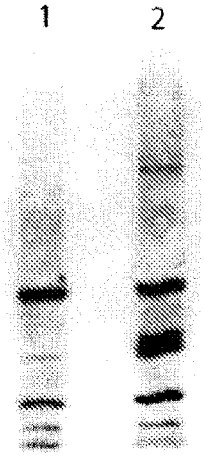
Figure 7:
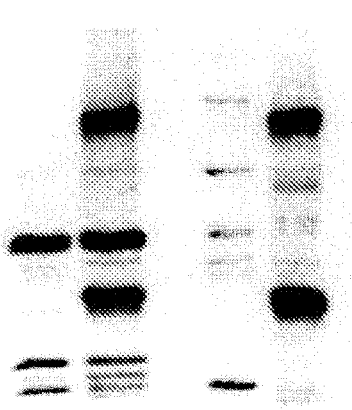

Expression of the recombinant dual tagged mouse HIF-1α cDNA Myc-HIF-6×His-V5 in the N2A neuroblastoma line demonstrated accumulation of V5 labeled HIF-1α 24 hours post-transfection (FIG. 7A). The V5-reactive C-terminal fragment of HIF-1α was detected only after treatment of transfected cells with the proteosome inhibitor MG132, indicating this species is labile under standard conditions. The addition of MKPwt reduced overall levels of both full-length and C-terminal fragments. Under similar conditions, the human HIF-1α fusion also produced the expected c-terminal HIF-1α fragment in the N2A line treated with MG132 (FIG. 7B). Using nickel affinity purification strategies, purification of the full length and c-terminal HIF-1α cleavage product away from contaminating protein species also reactive with the V5 antibody present in the crude lysates was demonstrated (FIG. 7C, compare purified product in lane 4 vs. crude sample in lane 2). Bands correlating to full length (approximately 110 kDa) and the c-terminal fragment (running at approximately 48 kDa) were isolated from polyacrylamide gels and subjected to LC-MS/MS. As shown peptides present in the full length (FIG. 8A) and the C-terminal fragment of HIF-1α were identified and mapped onto the full length sequence of human HIF-1α (826 AA). The LFAEDTEAK (SEQ ID NO:7) epitope discovered in the C-terminal fragment represents the minimum N-terminal start site for the c-terminal HIF-1α fragment suggesting the putative cleavage site exists upstream of HIF-1α AA538.

All of the features described herein (including any accompanying claims, abstract and drawings), and/or all of the steps of any method or process so disclosed, may be combined with any of the above aspects in any combination, except combinations where at least some of such features and/or steps are mutually exclusive. Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of identifying compounds as candidate drugs for treatment of hypoxic conditions, said method comprising:

providing a cell expressing Hypoxia-Inducible-Factor-1alpha (HIF-1α) wherein HIF-1α undergoes site-specific cleavage that generates paired HIF-1α fragments;

contacting the cell with a compound to be evaluated;

determining the ability of the compound to inhibit the site-specific cleavage of HIF-1α, wherein said determining involves detecting the presence of one or both of the paired HIF-1α fragments generated, wherein a decrease in the number of one or both of the paired HIF-1α fragments in the presence of the compound compared to when the compound is absent indicates the compound has the ability to inhibit the site-specific cleavage of HIF-1α; and selecting, based on said determining, compounds capable of reducing site-specific cleavage of HIF-1α as candidate drugs for treatment of hypoxic conditions.

2. The method according to claim 1, wherein the cell further expresses Mitogen activated protein Kinase Phosphatase-1 (MKP-1).

3. The method according to claim 2, wherein compounds are further selected based on their ability to enhance or suppress MKP-1 activity/expression in the cell.

4. The method according to claim 1, wherein the cell further expresses HIF-1α targets.

5. The method according to claim 4, wherein compounds are further selected based on their ability to down-regulate activity of the pro-apototic HIF-1α targets BNIP3 and Noxa.

6. The method according to claim 1, wherein the cell further expresses a protease known to cleave HIF-1α.

7. The method according to claim 1, wherein said site-specific cleavage occurs at two sites in HIF-1α.

8. The method according to claim 7, wherein said site-specific cleavage occurs between (i) amino acid residues 300-350 of HIF-1α and (ii) amino acid residues 477-539 of HIF-1α.

9. The method according to claim 7, wherein the paired HIF-1α fragments comprise, in one pair, a fragment of approximately 75 kDa, and in a second pair, a fragment of approximately 45 kDa.

10. The method according to claim 9, wherein said determining involves detecting the presence of the approximately 75 kDa fragment or a corresponding fragment of approximately 35 kDa.

11. The method according to claim 9, wherein said determining involves detecting the presence of the approximately 45 kDa fragment or a corresponding fragment of approximately 65 kDa.

12. The method according to claim 1, wherein said detecting is carried out using an antibody to one of the fragments.

13. The method according to claim 1, wherein said detecting involves Western blot analysis.

* * * * *